US010456018B2

(12) United States Patent
Hoshi et al.

(10) Patent No.: US 10,456,018 B2
(45) Date of Patent: Oct. 29, 2019

(54) FLEXIBLE TUBE AND INSERTION APPARATUS

(71) Applicant: OLYMPUS CORPORATION, Hachioji-shi, Tokyo (JP)

(72) Inventors: Naoyuki Hoshi, Aizuwakamatsu (JP); Takahiro Kishi, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 151 days.

(21) Appl. No.: 15/488,172

(22) Filed: Apr. 14, 2017

(65) Prior Publication Data

US 2017/0215712 A1    Aug. 3, 2017

Related U.S. Application Data

(63) Continuation of application No. PCT/JP2015/083798, filed on Dec. 1, 2015.

(30) Foreign Application Priority Data

Dec. 2, 2014   (JP) .................................. 2014-244358

(51) Int. Cl.
 *A61B 1/01*    (2006.01)
 *A61B 1/005*   (2006.01)
 (Continued)

(52) U.S. Cl.
 CPC ............... *A61B 1/01* (2013.01); *A61B 1/005* (2013.01); *A61B 1/0051* (2013.01);
 (Continued)

(58) Field of Classification Search
 CPC ....... A61B 1/01; A61B 1/00078; A61B 1/005; A61B 1/0051; F16L 11/12; G02B 23/2476
 (Continued)

(56) References Cited

U.S. PATENT DOCUMENTS 5,549,542 A *  8/1996  Kovalcheck ......... A61B 1/0052
                                              600/146
9,486,126 B2 * 11/2016  West ...................... A61B 1/018
(Continued)

FOREIGN PATENT DOCUMENTS

JP      S58-103431 A    6/1983
JP      2007236472 A    9/2007
(Continued)

OTHER PUBLICATIONS

Feb. 23, 2016 Search Report issued in International Patent Application No. PCT/JP2015/083798.
(Continued)

*Primary Examiner* — Craig M Schneider
*Assistant Examiner* — David R Deal
(74) *Attorney, Agent, or Firm* — Oliff PLC

(57) ABSTRACT

A flexible tube includes a helical tube having a first sparsely wound region, a closely wound region, a change region, and a second sparsely wound region. In a state where the change region is arranged between the closely wound region and the second sparsely wound region, the change region changes an unbendability such that the unbendability of the distal end portion of the third flexible portion is closer to the unbendability of the second flexible portion and the unbendability of the proximal end portion of the third flexible portion is closer to the unbendability of the fourth flexible portion.

11 Claims, 15 Drawing Sheets

(51) Int. Cl.
*F16L 11/12* (2006.01)
*G02B 23/24* (2006.01)
*A61B 1/00* (2006.01)

(52) U.S. Cl.
CPC .......... *A61B 1/00078* (2013.01); *F16L 11/12* (2013.01); *G02B 23/2476* (2013.01)

(58) Field of Classification Search
USPC ........................................................ 138/134
See application file for complete search history.

(56) References Cited

U.S. PATENT DOCUMENTS

| | | | | |
|---|---|---|---|---|
| 9,820,633 | B2* | 11/2017 | Iede | A61B 1/0055 |
| 9,820,688 | B2* | 11/2017 | Jenkins | A61B 1/00071 |
| 2009/0023989 | A1* | 1/2009 | Honda | A61B 1/00133 |
| | | | | 600/106 |
| 2009/0198103 | A1* | 8/2009 | Suzuki | A61B 17/00234 |
| | | | | 600/139 |
| 2013/0112457 | A1* | 5/2013 | Kitagawa | A61B 1/0056 |
| | | | | 174/68.3 |
| 2013/0144126 | A1* | 6/2013 | Iede | A61B 1/0055 |
| | | | | 600/139 |
| 2014/0155697 | A1 | 6/2014 | Iede | |
| 2014/0188081 | A1 | 7/2014 | Saito et al. | |

FOREIGN PATENT DOCUMENTS

| | | |
|---|---|---|
| JP | 2013-90717 A | 5/2013 |
| JP | 2013-097327 A | 5/2013 |
| JP | 2014-113320 A | 6/2014 |
| WO | 2013/168552 A1 | 11/2013 |
| WO | 2015/083644 A1 | 6/2015 |
| WO | WO-2015083645 A1 * | 6/2015 ........... A61B 1/0055 |

OTHER PUBLICATIONS

Jun. 6, 2017 International Preliminary Report on Patentability issued in International Patent Application No. PCT/JP2015/083798.

* cited by examiner

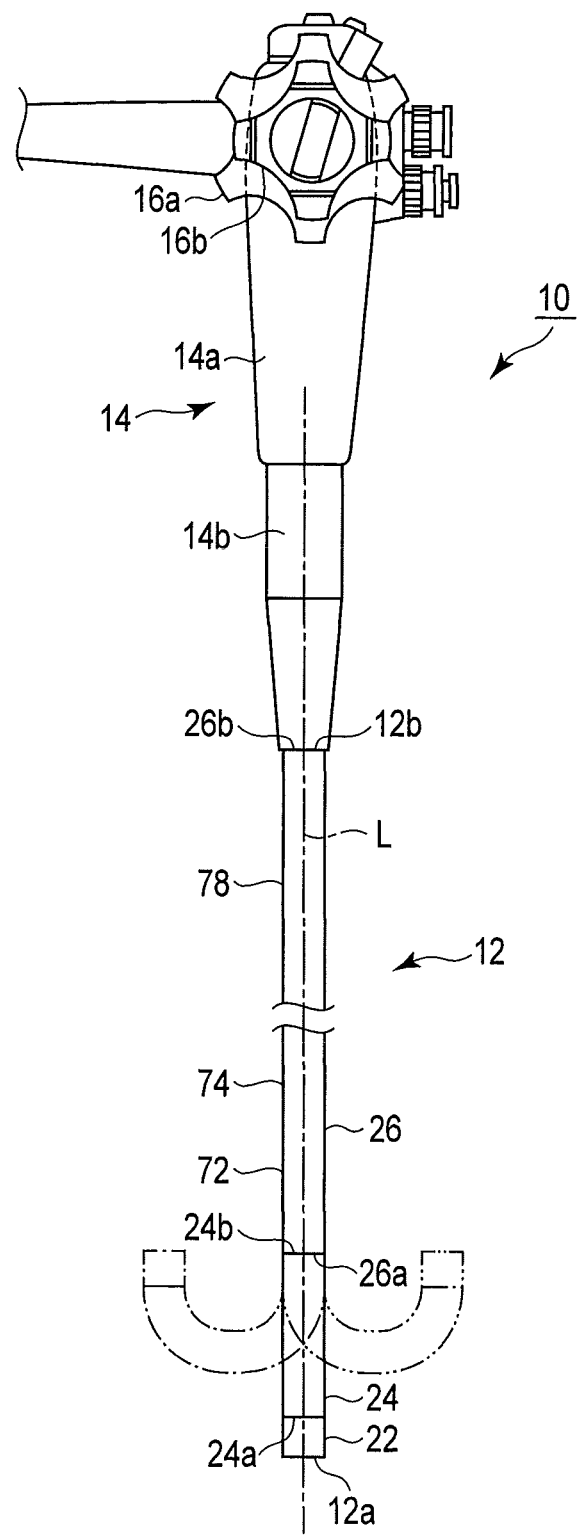
F I G. 1

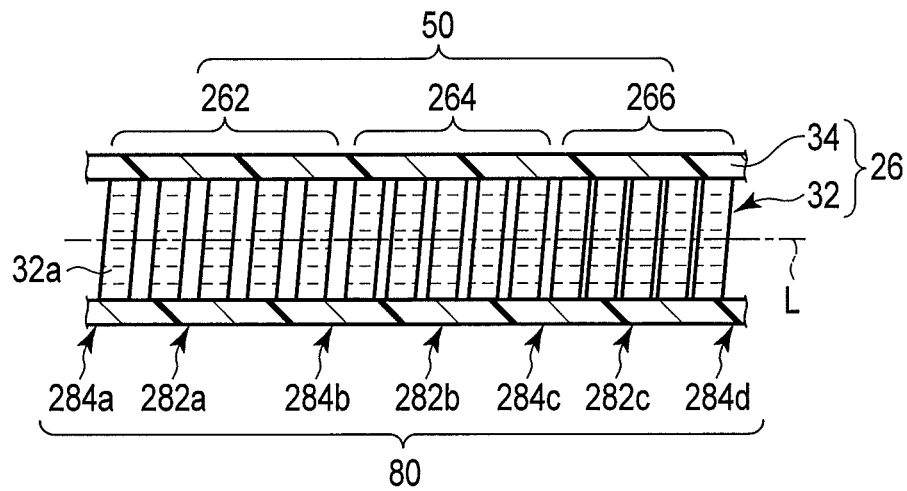
F I G. 13
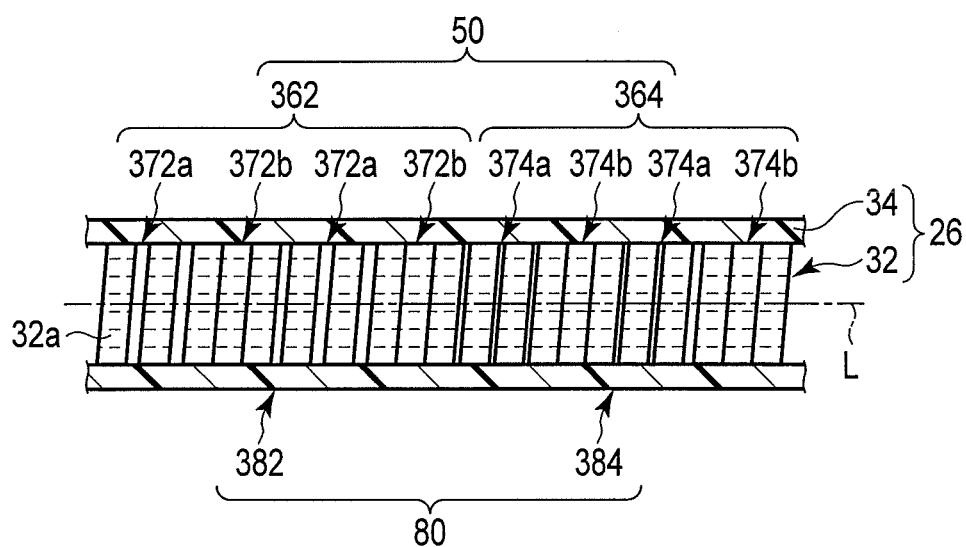
F I G. 14

FLEXIBLE TUBE AND INSERTION APPARATUS

CROSS-REFERENCE TO RELATED APPLICATIONS

This application is a Continuation application of PCT Application No. PCT/JP2015/083798, filed Dec. 1, 2015 and based upon and claiming the benefit of priority from prior Japanese Patent Application No. 2014-244358, filed Dec. 2, 2014, the entire contents of all of which are incorporated herein by reference.

BACKGROUND OF THE INVENTION

1. Field of the Invention

The present invention relates to a flexible tube of an insertion apparatus (e.g., an endoscope) which is inserted into a cavity of a passage, and also to an insertion apparatus having the flexible tube.

2. Description of the Related Art

A flexible tube made by providing an outer sheath on the outer side of a helical tube is disclosed, for example, in Jpn. Pat. Appln. KOKAI Publication No. 2013-097327. The helical tube of the flexible tube includes a closely wound region in which a closely wound portion and a sparsely wound portion are alternately arranged in the longitudinal direction. The closely wound portion is a portion where the wire portions adjacent in the longitudinal direction are applied with a tight contact force, and the sparsely wound portion is a portion where the wire portions adjacent in the longitudinal direction are separate from each other.

BRIEF SUMMARY OF THE INVENTION

According to one aspect of the present invention, a flexible tube defining a longitudinal axis by a distal end and a proximal end thereof, includes: a tubular outer sheath defining a length of the flexible tube; and a helical tube including: a first sparsely wound region arranged along the longitudinal axis, including adjacent wire portions of a wire member which are adjacent along the longitudinal axis and which are separate from each other, and cooperating with the outer sheath to form a first flexible portion; a closely wound region located closer to the proximal side than the first sparsely wound region along the longitudinal axis, the closely wound region including a plurality of closely wound portions that include adjacent wire portions of the wire member which are adjacent along the longitudinal axis applied with a tight contact force and which are in tight contact with each other, and a sparsely wound region which is arranged between the closely wound portions and in which the wire portions are separate from each other along the longitudinal axis, the closely wound region cooperating with the outer sheath to form a second flexible portion, the closely wound region being unbendable than the first sparsely wound region; a change region arranged along the longitudinal axis, cooperating with the outer sheath to form a third flexible portion, and changing unbendabilities between a distal end portion and a proximal end portion thereof; and a second sparsely wound region located closer to the proximal side than the closely wound region along the longitudinal axis, including adjacent wire portions of the wire member which are adjacent along the longitudinal axis and which are separate from each other, the second sparsely wound region being bendable than the closely wound region, and cooperating with the outer sheath to form a fourth flexible portion, wherein: in a state where the change region is arranged between the closely wound region and the second sparsely wound region, the change region changes an unbendability in cooperation with the outer sheath such that the unbendability of the distal end portion of the third flexible portion is closer to the unbendability of the second flexible portion and the unbendability of the proximal end portion of the third flexible portion is closer to the unbendability of the fourth flexible portion, and in a state where the change region is arranged between the first sparsely wound region and the closely wound region, the change region changes an unbendability in cooperation with the outer sheath such that the unbendability of the distal end portion of the third flexible portion is closer to the unbendability of the first flexible portion and the unbendability of the proximal end portion of the third flexible portion is closer to the unbendability of the second flexible portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view showing an endoscope, which is an example of an insertion apparatus according to the first to third embodiments;

FIG. 13 is a schematic longitudinal section illustrating part of the flexible tube of the insertion section of the insertion apparatus according to the second embodiment;

FIG. 14 is a schematic longitudinal section illustrating part of the flexible tube of the insertion section of the insertion apparatus according to a modification of the second embodiment.

DETAILED DESCRIPTION OF THE INVENTION

Figure 2:
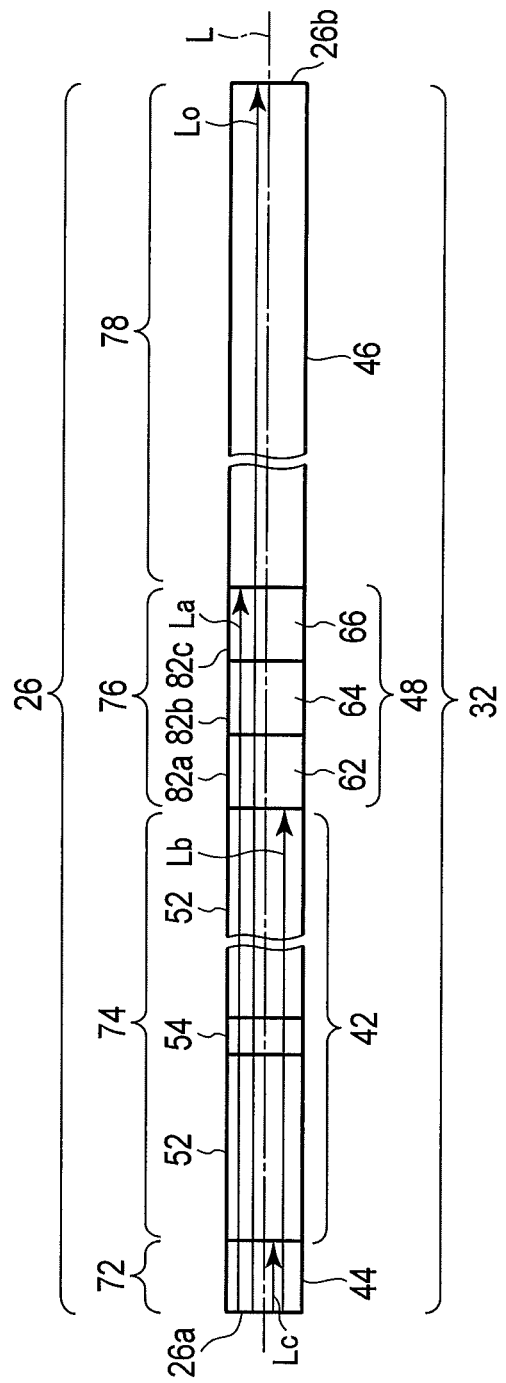
FIG. 2 is a schematic view showing a flexible tube of an insertion section of the insertion apparatus according to the first embodiment.

Hereinafter, embodiments of the present invention will be described with reference to the accompanying drawings.

The first embodiment will be described with reference to FIG. 1 to FIG. 4B.

A description will be given of the case where the insertion apparatus 10 of the embodiment is a medical endoscope. The insertion apparatus 10 may be suitably realized not only as a medical endoscope but also as an industrial endoscope, or an insertion apparatus having neither an illumination optical system nor an observation optical system (e.g., a catheter).

As shown in FIG. 1, the insertion apparatus 10 of the embodiment includes: an insertion section 12 having a distal end portion 12a and a proximal end portion 12b; and a grasp section (operation section) 14 located at the proximal end portion 12b of the insertion section 12. The grasp section 14 includes a grasp section main body 14a grasped by the user and an anti-break 14b. Through the anti-break 14b, the proximal end portion 12b of the insertion section 12 is coupled to the grasp section 14, so that the insertion section 12 is prevented from being bent (e.g., buckled) at the proximal end portion 12b thereof.

The distal end portion 12a and proximal end portion 12b of the insertion section 12 or the distal end 26a and proximal end 26b of a flexible tube 26 (mentioned below) define a longitudinal axis L, which is a central axis. Let us assume that the distance between the distal end 26a of the flexible tube 26 and the proximal end 26b thereof is Lo, as shown in FIG. 2.

As shown in FIG. 1, the insertion section 12 includes, from its distal end portion 12a to its proximal end portion 12b, a distal-end hard portion 22, a bending portion 24 and a flexible tube 26. The distal end 24a of the bending portion 24 is coupled to the distal-end hard portion 22. The distal end 26a of the flexible tube 26 is coupled to the proximal end 24b of the bending portion 24. The proximal end 26b of the flexible tube 26 is coupled to the anti-break 14b of the grasp section 14.

The bending portion 24 can be bent, for example, in four directions by operating the knobs 16a and 16b of the grasp section main body 14a.

Figure 3:
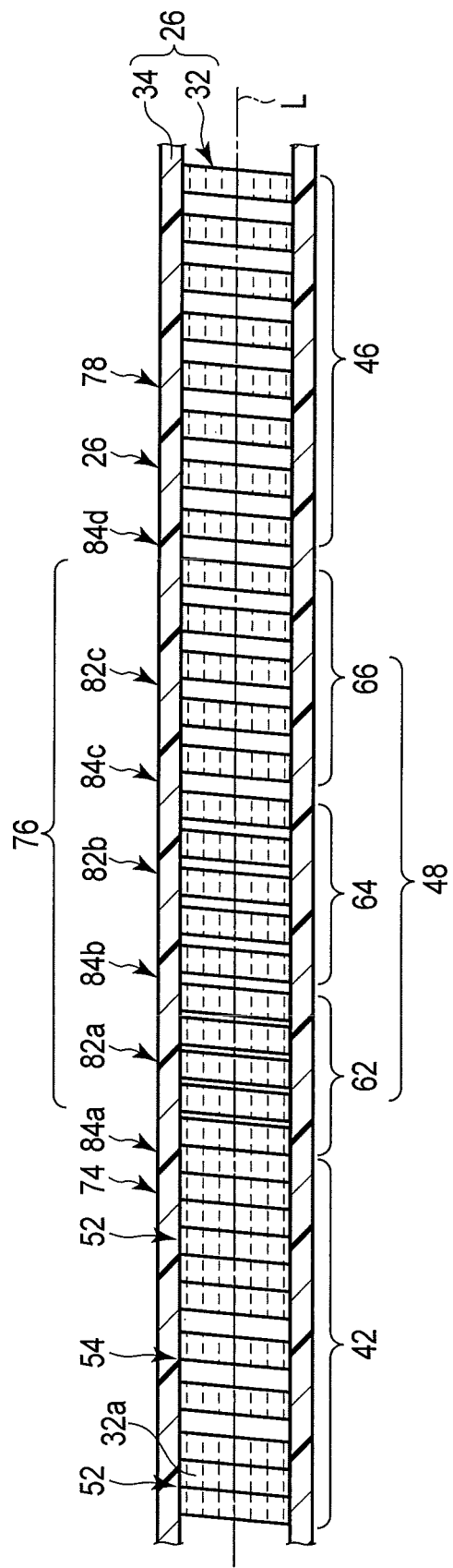
FIG. 3 is a schematic longitudinal section illustrating part of the flexible tube of the insertion section of the insertion apparatus according to the first embodiment.

As shown in FIG. 3, the flexible tube 26 includes a helical tube 32 and a tubular outer sheath 34 from radially inward to radially outward, with the central axis (longitudinal axis) L as a center. A tubular net-like blade (not shown) may be suitably arranged between the helical tube 32 and the outer sheath 34.

The helical tube 32 is formed by helical winding a wire member 32a, which is made of a metal such as stainless steel and may be in the form of an elongated band, around the longitudinal axis L. It is desirable that the outer and inner diameters of the helical tube 32 be constant or substantially constant from the distal end to the proximal end. The helical tube 32 is a spirally wound tubular member having an unbendability which is hard to bend in directions away from the longitudinal axis L (e.g., a direction perpendicular to the longitudinal direction) and a resiliency which tends to return to its original shape when the helical tube 32 is bent.

As shown in FIGS. 2 and 3, the helical tube 32 of the flexible tube 26 includes: a closely wound region (highly-resilient region) 42 arranged on the longitudinal axis L, a first sparsely wound region (a distal side sparsely wound region) 44 arranged at the distal side of the closely wound region 42, a second sparsely wound region (a proximal side sparsely wound region) 46 arranged at the proximal side of the closely wound region 42, and a proximal side change region (proximal side resilience-changing region) 48 arranged between the closely wound region 42 and the second sparsely wound region 46 and configured to change the unbendability and/or the resilience. The first sparsely wound region 44 (which is a normally resilient region having lower resilience than the highly resilient region) is shorter than the closely wound region 42, as measured along the longitudinal axis L. The first sparsely wound region 44 is shorter than the second sparsely wound region 46 (which is a normally-resilient region having lower resilience than the highly-resilient region), as measured along the longitudinal axis L.

In the present embodiment, the proximal end of the first sparsely wound region 44 is coupled directly to the distal end of the closely wound region 42, as shown in FIG. 2.

It is preferable that the total length La (<Lo) of the first sparsely wound region 44, closely wound region 42 and the change region 48 (which are from the distal side of the helical tube 32 of the flexible tube 26 to the proximal end of the helical tube) be equal to the length of the large intestine made linear greater, so that the insertion section 12 inserted from the anus can reach a deep portion of the large intestine.

Assuming that the insertion apparatus 10 is an endoscope used for the large intestine, the length (distance) Lb between the distal end 26a of the flexible tube 26 and the proximal end of the second flexible portion 74 is desirably 700 mm or so, and the length (distance) Lc (FIG. 2) between the distal end 26a of the flexible tube 26 and the distal end of the second flexible portion 74 is desirably in the range of 30 mm to 50 mm. It is desirable that a third flexible portion 76 (mentioned below) be in the range from tens of mm to 100 mm or so. These dimensional requirements are applicable to the embodiments and modifications mentioned below.

The total length of the first sparsely wound region 44, closely wound region 42 and change region 48 of the helical tube 32, as measured along the longitudinal axis L, namely the distance (length) La between the distal end 26a of the flexible tube 26 and the proximal end of the change region 48 (i.e., the distal end of the second sparsely wound region 46) is properly determined in accordance with a body portion to be examined.

The length of the first sparsely wound region 44 along the longitudinal axis L can be properly determined.

As shown in FIGS. 2 and 3, the closely wound region 42 includes a plurality of closely wound portions 53 and a plurality of sparsely wound portions 54, which are alternately arranged along the longitudinal axis L. In other words, each sparsely wound portion 54 is located between the adjacent closely wound portions 52. Where the closely wound portions 52 are three in number, the sparsely wound portions 54 are at least two in number. That is, needless to say, the sparsely wound portions 54 are desirably two or more.

In the closely wound region 42, each closely wound portion 52 is longer than a sparsely wound portion 54 along the longitudinal axis L. In the present embodiment, in the closely wound region 42, the total of the lengths of the closely wound portions 52 along the longitudinal axis L is larger than the total of the lengths of the sparsely wound portions 54 along the longitudinal axis L.

Figure 4A:
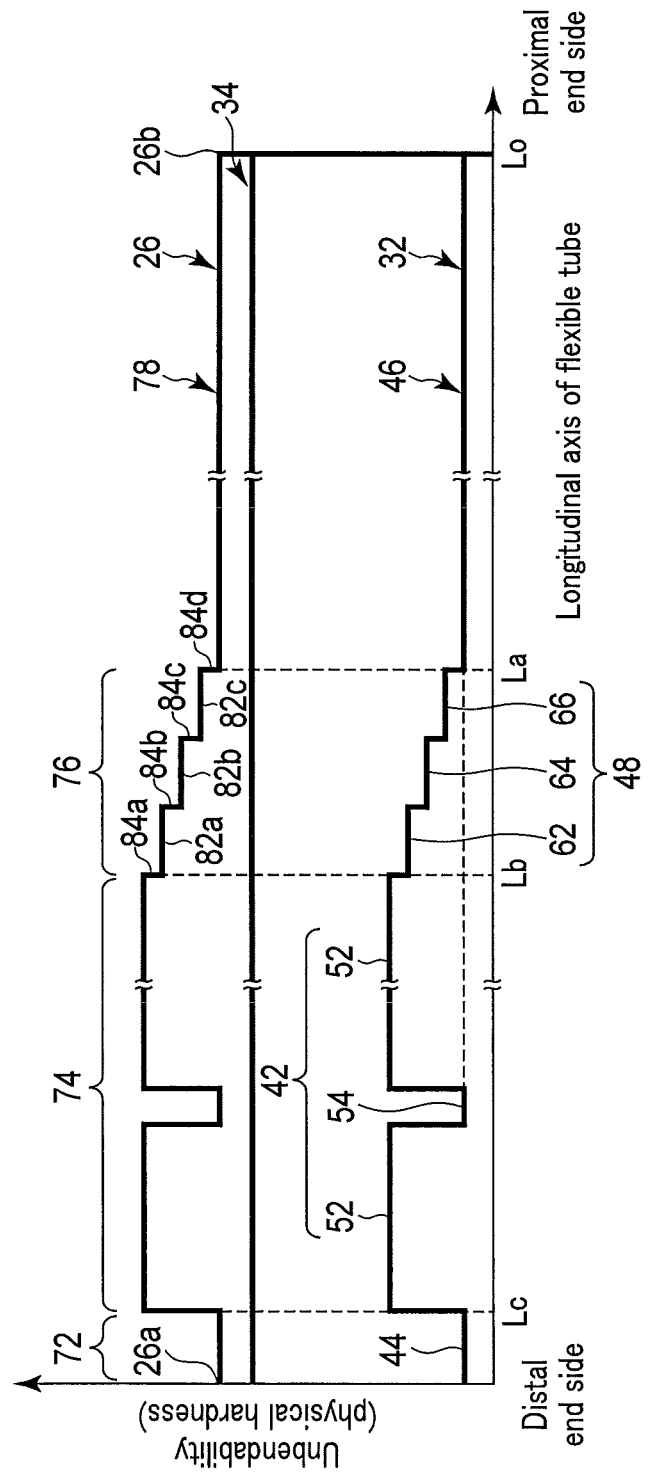
FIG. 4A is a schematic graph illustrating how the flexible tube, helical tube and outer sheath of the insertion section of the insertion apparatus of the first embodiment are hard to bend at positions along the longitudinal axis.
Figure 4B:
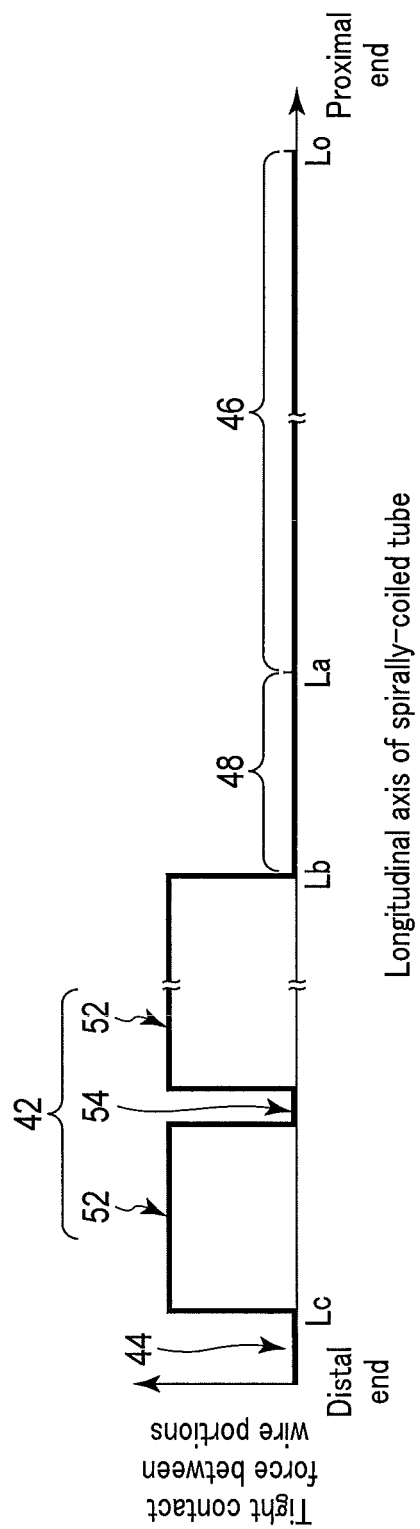
FIG. 4B is a schematic graph illustrating how the tight contact force between the adjacent parts of a wire member is at longitudinal positions of the helical tube of the flexible tube of the insertion section of the insertion apparatus of the first embodiment.

As shown in FIGS. 3 and 4B, each closely wound portion 52 is applied with such an initial tensile force as enables the adjacent wire portions 32a to be in close contact with each other along the longitudinal axis. Because of this initial tensile force, a tight contact force initial tensile force) as enables the wire portions 32a adjacent along the longitudinal axis L to be in tight contact with each other is imparted. The initial tensile force (tight contact force) to be applied can be properly adjusted, for example, by how the wire member 32a is wound. It is assumed here that the tight contact force with which the adjacent parts of the wire member 32a are in contact with each other because of the initial tensile force is substantially constant at each position along the longitudinal axis L. The tight contact force of the wire portions 32a can be varied by changing the structure of the winding or changing the width and plate thickness of the wire member 32a.

Where the longitudinal axis L of the closely wound portion 52 is vertical, the tight contact force maintains the state where the wire portions 32a of the closely wound portion 52 are in tight contact, against the force of gravity, and no gap is provided between the wire portions 32a. If an external force is applied toward the longitudinal axis L of the closely wound portion 52 where the longitudinal axis L is horizontal, no gap will be provided between the wire portions 32a until the external force exceeds the tight contact force. In this manner, the closely wound portion 52 is prevented from being bent. If the external force exceeds the tight contact force of the adjacent wire portions 32a, a gap is produced between the wire portions 32a of the closely wound portion 52. As a result, the closely wound portion 52 is bent undesirably. Therefore, the closely wound portion 52 has a large bending rigidity before the closely wound portion 52 begins to bend, because of the tight contact force applied to the wire portions adjacent along the longitudinal axis L. After being deprived of the tight contact force, the closely wound portion bends in accordance with the spring constant of the helical tube 32. As can be seen in FIGS. 4A and 4B, the tight contact force applied to the wire portions 32a is related to the unbendability of the helical tube 32. Therefore, once the closely wound portion 52 of the flexible tube 26 begins to bend when the insertion section 12 is inserted into a predetermined passage, the flexible tube 26 can be bent as if the closely wound portion 52 were not present, i.e., the closely wound portion 52 were like the sparsely wound portion 54.

In the state where the closely wound portion 52 is bent, the tight contact force between the adjacent wire portions 32a along the longitudinal axis L of the closely wound portion 52 helps exhibit the resilient force enabling the closely wound portion 52 to return to the original state. In other words, the tight contact force applied to the wire portions 32a corresponds to the resilience of the helical tube 32. In particular, where the gaps between the wire portions 32a of the closely wound portion 52 are narrow (i.e., the case where the radius of curvature of the closely wound portion 52 in the bent state is large), the closely wound portion 52 exhibits resilience higher than that of each sparsely wound portion 54.

As shown in FIG. 3, in each sparsely wound portion 54, the wire portions 32a adjacent along the longitudinal axis L are apart from each other by a proper distance (pitch). In other words, in the sparsely wound portion 54, the wire portions 32a are separate from each other, and a tight contact force is not applied between the wire portions 32a. As shown in FIG. 4A, therefore, the sparsely wound portion 54 can be bent in a direction away from the longitudinal direction (e.g., in a direction perpendicular to the longitudinal axis) more easily than the closely wound portion 52. In the sparsely wound portion 54, the intervals at which the wire portions 32a are arranged need not be constant; the intervals may be shortened or lengthen, depending upon the portions. The sparsely wound portion 54 can be bent, relative to the longitudinal axis L, more easily than first to third regions 62, 64 and 66 (maintaining regions mentioned below) of the change region 48 as well as the closely wound portion 52.

Each sparsely wound portion 54 has spring characteristics. Therefore, each sparsely wound portion 54 exhibit resilience by which the sparsely wound portion 54 returns to the original state from the bent state. Unlike the wire portions 32a of the closely wound portion 52, the wire portions 32a of each sparsely wound portion 54 are not applied with a tight contact force Therefore, the resilience of each sparsely wound portion 54 is lower than that of the closely wound portion 52.

In the present embodiment, the change region 48 is continuous with the most-proximal closely wound portion 52 of the closely wound region 42, as shown in FIG. 2 to FIG. 4B. In the change region 48, the distance between the wire portions 32a adjacent along the longitudinal axis L is adjusted such that the resilience (how easily the original linearity returns from a bent state) is decreased stepwise from the distal side to the proximal side, relative to the resilience of the proximal end of the closely wound portion 52.

As shown in FIGS. 2 and 3, the change region 48 includes first to three regions (proximal-side regions) 62, 64 and 66, which are continuous from the distal side to the proximal side along the longitudinal axis L.

In the first region 62 shown in FIG. 3, the intervals of the adjacent wire portions 32a are constant, so that the unbendability and resilience of the first region 62 are constant. Likewise, in the second region 64, the intervals of the adjacent wire portions 32a are constant, so that the unbendability and resilience of the second region 64 are constant. Likewise, in the third region 66, the intervals of the adjacent wire portions 32a are constant, so that the unbendability and resilience of the third region 66 are constant.

The intervals of the adjacent wire portions 32a of the first region 62 are shorter than those of the wire portions 32a of the sparsely wound portion 54 of the closely wound region 42. In the first region 62, the wire portions 32a may be brought into tight contact with each other, with a tight contact force applied. Alternatively, the wire portions 32a may be simply brought into contact with each other. Furthermore, the wire portions 32a of the first region 62 may be slightly separate from each other. As shown in FIG. 4A, the bending hardness and resilience (representing how easily the first region 62 returns to the original substantially linear state from a bent state) are lower than those of the closely wound portion 52 of the closely wound region 42, but are higher than those of the first sparsely wound region 44, the sparsely wound portion 54 of the closely wound region 42 and the second sparsely wound region 46. The unbendability and resilience of the first region 62 are constant.

In FIG. 3, the wire portions 32a of the first region 62 are shown slightly separate from each other.

As shown in FIG. 3, the intervals of the adjacent wire portions 32a of the second region 64 are longer than those of the adjacent wire portions 32a of the first region 62 but are shorter than those of the adjacent wire portions 32a of the third region 66. As shown in FIG. 4A, the unbendability and resilience are lower than those of the closely wound portion 52 of the closely wound region 42, but are higher than those of the first sparsely wound region 44, the sparsely wound portion 54 of the closely wound region 42 and the second sparsely wound region 46. In addition, the unbendability and resilience of the second region 64 are lower than those of the first region 62 and are constant.

As shown in FIG. 3, the intervals of the adjacent wire portions 32a of the third region 66 are longer than those of the adjacent wire portions 32a of the first and second regions 62 and 64. The intervals of the adjacent wire portions 32a of the third region 66 are shorter than those of the wire portions 32a of the sparsely wound portion 54 of the closely wound region 42 and those of the wire portions 32a of the second sparsely wound region 46. As shown in FIG. 4A, the unbendability and resilience of the third region 66 are lower than those of the closely wound portion 52 of the closely wound region 42, but are higher than those of the sparsely wound portion 54. In addition, the bending hardness and resilience of the third region 66 are lower than those of the first and second regions 62 and 64. The unbendability and resilience of the third region 66 are lower than those of the first and second sparsely wound regions 44 and 46. The unbendability and resilience of the third region 66 are constant.

As described above, the change region 48 of the helical tube 32 is configured such that the unbendability and resilience of the distal end portion are set close to those of the closely wound region 42 and the unbendability and resilience of the proximal end portion are set to be close to those of the second sparsely wound region 46. To be more specific, the unbendability of the change region 48 of the helical tube 32 is decreased stepwise and the resilience thereof is lowered stepwise from the distal side to the proximal side, with the unbendability and resilience of the most proximal closely wound portion 52 of the closely wound region 42 as basic values. The unbendability and resilience of the change region 48 are made closer to those of the second sparsely wound region 46 stepwise.

It is preferable that the first sparsely wound region 44 and the second sparsely wound region 46 be formed similar to the second sparsely wound portion 54 of the closely wound region 42. In the first sparsely wound region 44 and the second sparsely wound region 46, the adjacent wire portions 32a adjacent along the longitudinal axis L are apart from each other by a proper distance (pitch). In the first and second sparsely wound regions 44 and 46, the adjacent wire portions 32a are separate from each other, and a tight contact force is not applied between the adjacent wire portions 32a (see FIG. 4B). Owing to this feature, the first sparsely wound region 44 and the second sparsely wound region 46 can be bent more easily than the closely wound portion 52 when an external force is applied thereto in a direction away from the central axis L (e.g., a direction perpendicular to the central axis L). The first sparsely wound region 44 and the second sparsely wound region 46 can be bent more easily than the closely wound portion 52 and the change region 48. The second sparsely wound region 46 is longer than the first sparsely wound region 44. In other words, the first sparsely wound region 44 is shorter than the second sparsely wound region 46 along the longitudinal axis L.

When the helical tube 32 is made, the first sparsely wound region 44, the closely wound portion 52 and sparsely wound portion 54 of the closely wound region 42, the change region 48 and further the second sparsely wound region 46 may be integrally formed. Alternatively, a first helical tube in which the first sparsely wound region 44 and the closely wound portion 52 and sparsely wound portion 54 of the closely wound region 42 are integrally formed, a second helical tube in which the change region 48 is formed, and a third spirally-coiled in which the second sparsely wound region 46 is formed, may be welded together, thereby fabricating a single helical tube 32.

The outer sheath 34 depicted in FIG. 3 is a tubular member formed, for example, by extrusion molding and made of a resin material that does not much extend or shrink in the direction of the longitudinal axis L. The unbendability and resilience of the outer sheath 34 can be properly determined. It is preferable that the resin material forming the outer sheath 34 be heat- and chemical-resistant and can be repeatedly cleaned and sterilized. It is also preferable that the resin material be electrically insulative (non-conductive).

The outer sheath 34 covers the outer circumference of the helical tube 32 and extends throughout the overall length of the helical tube 32. The outer sheath 34 defines the length of the flexible tube 26. It is assumed here that the unbendability and resilience of the outer sheath 34 are constant from the distal end to the proximal end.

With this structure, the outer sheath 34 defines the overall length Lo of the flexible tube 26, and the overall length Lo of the helical tube 32 is prevented from varying. Let us assume that the overall length of the helical tube 32 does not vary and that an external force is applied to the closely wound region 42 in a direction away from the longitudinal axis L (e.g., a direction perpendicular to the longitudinal axis). In this case, the sparsely wound portion 54 functions as a buffer and the closely wound region 42 is bent. That is, the closely wound portion 52 can be bent at any position, with the gaps between the wire portions 32a of the sparsely wound portion 54 being decreased.

When the closely wound region 42 is bent, the sparsely wound portion 54 absorbs the extension of the helical tube 32 along the longitudinal axis L, which is caused when the closely wound portion 52 extends along the longitudinal axis L in the axial direction of the helical tube 32. Therefore, the sparsely wound portion 54 of the closely wound region 42 cancels the extension of the helical tube 32 along the longitudinal axis L. Since the closely wound region 42 includes not only the closely wound portion 52 but also the sparsely wound portion 54, it can be smoothly bent, with the characteristics of the closely wound portion 52 maintained (the closely wound portion 52 has higher spring characteristics (resilience) than those of the sparsely wound portion 54). Because of the resilience based on the tight contact force of the closely wound portion 52, the closely wound region 42 can be restored to the substantially linear state from a bent state, with the total length maintained by the outer sheath 34.

Not only when an external force is applied to the closely wound portion 52 of the closely wound region 42 but also when it is applied to the sparsely wound portion 54, the closely wound region 42 is bent such that the sparsely wound portion 54 to which the external force is applied and other sparsely wound portions 54 function as an absorber. Like the sparsely wound portion 54 of the closely wound region 42, the sparsely wound region 44 is also allowed to function as an absorber.

The first sparsely wound region 44 of the helical tube 32 and the outer sheath 34 on the outer side of the first sparsely wound region 44 cooperate with each other, and a first flexible portion 72 is formed thereby. The closely wound region 42 of the helical tube 32 and the outer sheath 34 on the outer side of the closely wound region 42 cooperate with each other, and a second flexible portion 74 is formed thereby. The change region 48 of the helical tube 32 and the outer sheath 34 on the outer side of the change region 48 cooperate with each other, and a third flexible portion 76 is formed thereby. The second sparsely wound region 46 of the helical tube 32 and the outer sheath 34 on the outer side of the second sparsely wound region 46 cooperate with each other, and a fourth flexible portion 78 is formed thereby. That is, the flexible tube 26 of the present embodiment includes, from the distal side to the proximal side along the longitudinal axis L, the first flexible portion 72, the second flexible portion 74, the third flexible portion 76 and the fourth flexible portion 78.

Roughly speaking, the unbendability of the first flexible portion 72 can be regarded as the sum of the unbendability of the first sparsely wound region 44 and the unbendability of the outer sheath 34 (the first sparsely wound region 44 is located on the longitudinal axis L and radially inward, and the outer sheath 34 is located radially outward), as can be seen in FIG. 4A. Roughly speaking, the resilience of the first flexible portion 72 can be regarded as the sum of the resilience of the first sparsely wound region 44 and the resilience of the outer sheath 34 (the first sparsely wound region 44 is located on the longitudinal axis L and radially inward, and the outer sheath 34 is located radially outward). The unbendability and resilience of the first flexible portion 72 are substantially constant.

Roughly speaking, the unbendability of the second flexible portion 74 can be regarded as the sum of the unbendability of the closely wound portion 52 of the closely wound region 42 of the helical tube 32 and the unbendability of the outer sheath 34 or as the sum of the unbendability of the sparsely wound portion 54 and the unbendability of the outer sheath 34 (the closely wound portion 52 is located on the longitudinal axis L and radially inward, and the outer sheath 34 is located radially outward). That is, the unbendability of the second flexible portion 74 can be regarded as the sum of the unbendability of the closely wound region 42 and the unbendability of the outer sheath 34. Roughly speaking, the resilience of the second flexible portion 74 can be regarded as the sum of the resilience of the closely wound portion 52 of the closely wound region 42 of the helical tube 32 and the resilience of the outer sheath 34 or as the sum of the resilience of the sparsely wound portion 54 and the resilience of the outer sheath 34. That is, the resilience of the second flexible portion 74 can be regarded as the sum of the resilience of the closely wound region 42 and the resilience of the outer sheath 34. From a microscopic point of view, the unbendability and resilience of the second flexible portion 74 vary depending upon positions, i.e., a position where the closely wound portion 52 is provided and a position where the sparsely wound portion 54 is provided. From a macroscopic point of view, the unbendability and resilience of the second flexible portion 74 are constant, because the outer sheath 34 is provided on the closely wound region 42. The user of the insertion apparatus 10 can regard the unbendability and resilience of the second flexible portion 74 as being constant when using the flexible tube 26. This is attributable to the fact that sparsely wound portion 54 is shorter than the closely wound portion 52.

Roughly speaking, the unbendability of the third flexible portion 76 can be regarded as the sum of the unbendability of the change region 48 of the helical tube 32 and the unbendability of the outer sheath 34 (the change region 48 is located on the longitudinal axis L and radially inward, and the outer sheath 34 is located radially outward). Roughly speaking, the resilience of the third flexible portion 76 can be regarded as the sum of the resilience of the change region 48 of the helical tube 32 and the resilience of the outer sheath 34 (the change region 48 is located on the longitudinal axis L and radially inward, and the outer sheath 34 is located radially outward).

From a microscopic point of view, the unbendability and resilience of the third flexible portion 76 vary depending upon positions, i.e., a position where the first region 62 is provided (i.e., a first portion 82a described later), a position where the second region 64 is provided (i.e., a second portion 82b described later), and a position where the third region 66 is provided (i.e., a third portion 82c described later). With this structure, the unbendability and resilience of the third flexible portion 76 decrease stepwise from the distal end to the proximal end. From a macroscopic point of view, the unbendability and resilience of the third flexible portion 76 decrease substantially linearly from the distal end to the proximal end, because the outer sheath 34 is provided on the change region 48. The user of the insertion apparatus 10 can regard the unbendability and resilience of the second flexible portion 74 as decreasing linearly when using the flexible tube 26. This is attributable to the fact that the third flexible portion 76 is comparatively short, and therefore first to third reduction portions 84a, 84b, 84c and 84d (described below) are shorter than the first to third portions 82a, 82b and 82c and provide a small amount of reduction effect.

Roughly speaking, the unbendability of the fourth flexible portion 78 can be regarded as the sum of the unbendability of the second sparsely wound region 46 of the helical tube 32 and the unbendability of the outer sheath 34 (second sparsely wound region 46 is located on the longitudinal axis L and radially inward, and the outer sheath 34 is located radially outward). Roughly speaking, the resilience of the fourth flexible portion 78 can be regarded as the sum of the resilience of the second sparsely wound portion 46 of the helical tube 32 and the resilience of the outer sheath 34 (second sparsely wound portion 46 is located on the longitudinal axis L and radially inward, and the outer sheath 34 is located radially outward). The unbendability and resilience of the fourth flexible portion 78 are substantially constant.

The first flexible portion 72 and the fourth flexible portion 78 are comparatively easy to bend. The first flexible portion 72 is easier to bend than the second flexible portion 74. The third flexible portion 76 is easier to bend than the second flexible portion 74, and is harder to bend than the distal end portion of the fourth flexible portion 78. In other words, in the present embodiment, the third flexible portion 76 is formed between the second flexible portion 74 and the fourth flexible portion 78 such that the unbendability/easiness of the third flexible portion 76 are intermediate between those of the second and fourth flexible portions 74 and 78.

The third flexible portion 76 includes, from the distal side to the proximal side, a first portion (maintaining region) 82a which is easier to bend than the second flexible portion 74 and keeps a proper unbendability, a second portion (maintaining region) 82b which is easier to bend than the first portion 82a and keeps a proper unbendability, and a third portion (maintaining region) 82c which is easier to bend than the second portion 82b and keeps a proper unbendability.

The third flexible portion 76 includes a first reduction portion 84a located between the proximal end of the second flexible portion 74 and the distal end of the first portion 82a of the third flexible portion 76. The first reduction portion 84a reduces the unbendability and the resilience of the proximal end of the second flexible portion 74 to those of the first portion 82a. The difference between the unbendability and the resilience of the proximal end of the closely wound portion 52 of the closely wound region 42 of the helical tube 32 and those of the distal end of the first region 62 of the change region 48 appears in the first reduction portion 84a.

The third flexible portion 76 includes a second reduction portion 84b located between the proximal end of the first portion 74 and the distal end of the second portion 82b. The second reduction portion 84b reduces the unbendability and the resilience of the first portion 82a to those of the second portion 82b. The difference between the unbendability and the resilience of the proximal end of the first region 62 of the helical tube 32 and those of the distal end of the second region 64 of the helical tube 32 appears in the second reduction portion 84b.

The third flexible portion 76 includes a third reduction portion 84c located between the proximal end of the second portion 82b and the distal end of the third portion 82c. The third reduction portion 84c reduces the unbendability and resilience of the second portion 82b to those of the third portion 82c. The difference between the unbendability and resilience of the proximal end of the second region 64 of the helical tube 32 and those of the distal end of the third region 66 of the helical tube 32 appears in the third reduction portion 84c.

The third flexible portion 76 includes a fourth reduction portion 84d located between the proximal end of the third portion 82c and the distal end of the third flexible portion 78. The fourth reduction portion 84d reduces the unbendability and resilience of the third portion 82c to those of the fourth flexible portion 78. The difference between the unbendability and resilience of the proximal end of the third region 66 of the helical tube 32 and those of the distal end of the second sparsely wound region 46 of the helical tube 32 appears in the fourth reduction portion 84d.

From a microscopic point of view, the unbendability and the resilience of the third flexible portion 76 are constant in the respective first portion 82a, second portion 82b and third portion 82c. From a macroscopic point of view, the unbendability and resilience of the third flexible portion 76 decrease substantially linearly from the distal end to the proximal end.

The first reduction portion 84a between the proximal end of the second flexible portion 74 and the distal end of the third flexible portion 76 is short. Therefore, the unbendability and resilience of the first portion 82a are prevented from decreasing to those of the first and fourth flexible portions 72 and 78. The second reduction portion 84b between the proximal end of the first portion 82a and the distal end of the second portion 82b is short. Therefore, the unbendability and resilience of the second portion 82b are prevented from decreasing to those of the first and fourth flexible portions 72 and 78. The third reduction portion 84c between the proximal end of the second portion 82b and the distal end of the third portion 82c is short. Therefore, the unbendability and resilience of the third portion 82c are prevented from decreasing to those of the first and fourth flexible portions 72 and 78.

As can be seen, the unbendability of the distal end portion of the third flexible portion 76 is made close to the unbendability of the proximal end portion of the second flexible portion 74, and the unbendability of the proximal end portion of the third flexible portion 76 is made close to the unbendability of the distal end portion of the fourth flexible portion 78. In the third flexible portion 76, the unbendability and resilience are gradually decreased, from the distal side to the proximal side along the longitudinal direction, from the unbendability and resilience of the second flexible portion 74 toward those of the fourth flexible portion 78.

The second flexible portion 74 has a higher resilience than those of the third and fourth flexible portions 76 and 78. The first flexible portion 72 is easier to bend than the second flexible portion 74, and the second flexible portion 74 is more resilient than the third and fourth flexible portions 76 and 78 (i.e., the second flexible portion 74 can easily return to the substantially linear state from a bent state). Therefore, even if the second flexible portion 74 is bent, it can return to the substantially linear state more easily than the third and fourth flexible portions 76 and 78.

The third flexible portion 76 is easier to bend than the second flexible portion 74, and is harder to bend than the fourth flexible portion 78. That is, the third flexible portion 74 adjusts the unbendability such that the difference between the unbendability of the second flexible tube 74 and the unbendability of the fourth flexible tube 78 decreases.

A description will be given of how the insertion apparatus 10 of the present embodiment operates.

The user of the insertion apparatus 10 holds the grasp section 14 and the first and second flexible portions 72 and 74 of the flexible tube 26. Then, the user inserts the distal-end hard portion 22, the bending portion 24 and the flexible tube 26 in this order into a narrow and curved passage, such as the large intestine. The user operates the knobs 16a and 16b to curve the bending portion 24, and changes the held positions of the flexible tube 26 gradually toward the proximal end, thereby permitting the insertion section 12 to be inserted into the passage.

The first flexible portion 72 is easier to bend than the second flexible portion 74. The second flexible portion 74 is easier to bend than the first flexible portion 72, and the unbendability of the second flexible portion 74 is determined such that the second flexible tube can be bent when an external force is applied by the inner circumference (inner wall) of the curved portion of the large intestine.

When the insertion section 12 is inserted from the hole (the anus) of a flexible passage (the large intestine) to a deep position (a deep portion of the large intestine), an external force (including a force of gravity) is applied from the inner circumferential surface (the inner wall) of the passage to the first and second flexible portions 72 and 74. The external force is applied in a direction away from the longitudinal axis L (e.g., in a direction perpendicular to the longitudinal axis L). If the applied external force is smaller than the unbendability of the first flexible portion 72, the first flexible portion 72 is not bent and remains linear. Likewise, if the applied external force is smaller than the unbendability of the second flexible portion 74, the second flexible portion 74 is not bent and remains linear. In this state, the second flexible portion 74 is inserted into the passage.

If the external force (including the force of gravity) applied from the inner circumferential surface exceeds the unbendability of the first flexible portion 72, the first flexible portion 72 begins to bend from the substantially linear state. That is, the first flexible portion 72 changes from the substantially linear state to a bent state.

For example, when the distal end portion 12a of the insertion section 12 is inserted from the anus to a deep portion of the large intestine, the first flexible portion 72 is bent along the inner circumferential surface of the passage. The second flexible portion 74 is also bent by the external force applied from the inner circumferential surface of the passage and exceeding the unbendability of the second flexible portion 74. Thus, the insertion section 12, including the first and second flexible portions 72 and 74, bends along the curve of the flexible passage (the large intestine).

The second flexible portion 74 has a higher resilience than the first flexible portion 72. Because of this resilience, the second flexible portion 74 can return to the substantially linear state from a bent state more easily than the first flexible portion 72. After the first flexible portion 72 passes a curve of the passage, the second flexible portion 74 makes the curve of the passage substantially linear because of its resilience. After the second flexible portion 74 is bent, the insertion section 12 is pulled back a little such that the external force applied to the second flexible portion 74 is reduced. In this manner, the second flexible portion 74 is allowed to easily exhibit its resilience. Because of this, a passage having a small radius of curvature, such as the sigmoid colon, can be made substantially linear. Since the first flexible portion 72 is also resilient, it returns to a substantially linear state. Then, the substantially-linear flexible tube 26 can easily pass through the substantially-linear passage. In this manner, the distal end 12a of the insertion section 12 can be inserted up to a deep portion of the passage.

After the first and second flexible portions 72 and 74 are sequentially bent and the first flexible portion 72 passes the curve of the passage, the passage is made substantially linear by utilization of the resilience of the second flexible portion 74. By doing so, a so-called stick phenomenon is prevented, in which the inner wall of the large intestine gets stuck with the distal end portion 12a of the insertion section 12 or the distal end 26a of the flexible tube 26.

In this manner, the first and second flexible portions 72 and 74 of the flexible tube 26 are properly bent in response to the external force applied from the inner circumferential surface of the passage, and the passage is made substantially linear by utilization of the second flexible portion 74. By repeatedly performing these operations, the distal end portion 12a of the insertion section 12 is made to move to a deep portion of the passage.

Let us assume that when the distal end portion 12a of the insertion section 12 has been inserted to a deep portion of the passage, the proximal end of the second flexible portion 74 of the flexible tube 26 (the proximal end is located at the position away from the distal end 26a of the flexible tube 26 by distance Lb (FIGS. 2, 4A and 4B) is more proximal than the hole (the anus) of the passage (i.e., the proximal end of the second flexible portion 74 is outside the body of the examinee). More specifically, let us assume that the proximal end of the second flexible portion 74 is located in the vicinity of the hole (the anus) of the passage. If an affected portion is at a further deeper position, the user holds the third flexible portion 76 and/or the fourth flexible portion 78 and inserts the insertion section 12 into the passage to move the distal end portion 12a of the insertion section 12 to the further deeper position. It should be noted here that the third flexible portion 76 enables the unbendability (bending hardness) to gently vary between the proximal end of the second flexible portion 74 and the distal end of the fourth flexible portion 78. That is, by the first to fourth reduction portions 84a, 84b, 84c and 84d of the third flexible portion 76, the unbendability is made to gently change stepwise along the longitudinal axis L between the proximal end of the second flexible portion 74 and the distal end of the fourth flexible portion 78. With this structure, the unbendability along the longitudinal axis L does not change greatly, unlike the case where the distal end of the fourth flexible portion 78 is connected directly to the proximal end of the second flexible tube 74.

Therefore, the portion between the proximal end of the second flexible portion 74 and the distal end of the fourth flexible portion 78 is prevented from being bent undesirably or permanently. When the insertion section 12 is pushed further into the passage, a force can be reliably transmitted, by way of the third flexible portion 76, to the proximal end of the second flexible portion 74 from the held position of the third flexible portion 76 and/or the fourth flexible portion 78, and this advantage cannot be expected in the case where the fourth flexible portion 78 is connected directly to the proximal end of the second flexible portion 74. In other words, because the third flexible portion 76 is provided, the force which the user applies when the third flexible portion 76 and/or the fourth flexible portion 78 of the flexible tube 26 is pushed along the longitudinal axis L is reliably transmitted to the distal end 26a of the first flexible portion 72 by way of the third flexible portion 76 and the second flexible portion 74.

Since the third flexible portion 76 is arranged between the second flexible portion 74 and the fourth flexible portion 78, an advancing force applied along the longitudinal axis L from any position on the proximal side of the proximal end of the second flexible portion 74 of the flexible tube 26 does not cause undesirable or permanent bending at that position. Therefore, the amount of operation at the third flexible portion 76 and/or fourth flexible portion 78 held by the right hand of the user of the insertion apparatus 10 is easily transmitted to the distal end 26a of the flexible tube 26 (namely, the distal end of the first flexible portion 72), and the flexible tube 26 can be easily inserted into a deep portion of the passage. That is, the distal end portion 12a of the insertion section 12 can be easily inserted to a deep portion of the passage.

As described above, the insertion apparatus 10 of the present embodiment has the following features:

The flexible tube 26 of the present embodiment includes a helical tube 32 and an outer sheath 34 covering the outer side of the helical tube 32, and the helical tube 32 includes a change region 48 located between the proximal end of the closely wound region 42 and the second sparsely wound region 46 and configured to decrease the unbendability and the resilience stepwise along the longitudinal axis L. The change region 48 of the helical tube 32 is intended to prevent the unbendability and resilience from having a large difference between the closely wound region 42 of the helical tube 32 and second sparsely wound region 46. The change region 48 includes a plurality of maintaining regions 62, 64 and 66 in which respective resiliences are maintained. The change region 48 decreases the unbendability and the resilience stepwise along the longitudinal axis L in a direction away from a position in the neighborhood of the closely wound region 42. In the present embodiment, the change region 48, which decreases the unbendability and resilience stepwise from the distal side to the proximal side, is arranged at the proximal end of the closely wound region 42 of the helical tube 32. The change region 48 forms part of the third flexible portion 76 that gradually changes the unbendability and resilience between the second flexible portion 74 and the fourth flexible portion 78 from the distal side to the proximal side such that the unbendability and resilience of the second flexible portion 74 gradually decrease to those of the fourth flexible portion 78.

In the present embodiment, the third flexible portion 76 including the change regions 48 varies the unbendability such that the unbendability at the distal end portion thereof is close to that of the second flexible portion 74 including the closely wound region 42 and such that the unbendability at the proximal end thereof is close to that of the fourth flexible portion 78 including the second sparsely wound region 46. The third flexible portion 76 decreases the resilience of the second flexible portion 74 stepwise from the distal side to the proximal side such that the resilience of the second flexible portion 74 becomes closer to the resilience of the fourth flexible portion 78.

The third flexible portion 76, especially the change region 48 thereof, enables the unbendability and resilience to change gently, unlike the case where the distal end of the third flexible portion 76 is arranged at the proximal end of the first flexible portion 72. When the user inserts the insertion section 12, namely the flexible tube 26, to a deep portion of the passage, while holding the third flexible portion 76 and/or the fourth flexible portion 78, the force applied by the user can be reliably transmitted to the distal end 26a of the flexible tube 26. That is, when the user inserts the insertion section 12, namely the flexible tube 26, to a deep portion of the passage, while holding the third flexible portion 76 and/or the fourth flexible portion 78, the third flexible portion 76 between the distal end of the fourth flexible portion 78 and the proximal end of the second flexible portion 74 is prevented from being bent undesirably or permanently, and the distal end portion of the fourth flexible portion 78 is prevented from being bent undesirably or permanently.

Since the unbendability of the portion between the second flexible portion 74 and the fourth flexible portion 78 is adjusted by the third flexible portion 76 including the change region 48, the pushing force with which the flexible tube 26 is inserted into the passage can be easily transmitted from the third flexible portion 76 and/or the fourth flexible portion 78 to the distal end 26a of the first flexible portion 72.

Since the second flexible portion 74 including the closely wound region 42 is arranged on the distal end portion side of the flexible tube 26, desirable bending characteristics and desirable resilience are exhibited in response to an external force applied to the passage. Therefore, the flexible tube 26 of the insertion section 12 bends in accordance with a curve of the flexible passage, such as the large intestine, and after the second flexible portion 74 passes the curve of the passage, the curve of the passage is made substantially linear by utilization of the resilience of the flexible tube 26 (the property of returning to the original linear state from the bent state), and the insertion section 12 can be inserted further into the passage. As described above, the flexible tube 26 of the present embodiment can easily make the passage substantially linear, as compared with a flexible tube having low resilience.

The present embodiment can provide a flexible tube 26 which can be easily inserted into a deep portion of a passage, and can also provide an insertion apparatus 10 having such a flexible tube 26.

Incidentally, the large intestine is a long organ having a number of curves. When the insertion section 12 of the insertion apparatus 10 is inserted into the large intestine, it has to bend in accordance with the curves of the large intestine. However, if the insertion section 12 is simply pushed in accordance with the curves, the large intestine may be extended excessively. In addition, a long time may be required for the insertion section 12 to pass through the curves and reach the appendix. If the large intestine is extended greatly, the insertion section 12 may not reach the appendix. As a technique for inserting the insertion section 12 into the large intestine, a curve of the large intestine is made substantially linear by utilization of the resilience of the flexible tube 26 (the property of returning to the original linear state from a bent state). In order to facilitate the insertion of the insertion section 12 into the large intestine, the use of a flexible tube 26 having high resilience is effective in making the large intestine substantially linear. In the closely wound region 42 of the flexible tube 26 of the present embodiment, the wire portions 32a of the helical tube 32 are applied with an initial tensile force (tight contact force) acting along the longitudinal axis L. The resilience can be enhanced thereby, and the insertion into the large intestine can be facilitated.

The relation between the unbendability of the helical tube 32 and the unbendability of the outer sheath 34 can be properly determined. That is, the outer sheath 34 may be designed to be harder to bend than the helical tube 32; conversely, the outer sheath 34 may be designed to be easier to bend than the helical tube 32. The unbendability of the outer sheath 34 may be partially changed along the longitudinal axis L, as will be described in connection with the second modification (see FIG. 6).

Although the change region 48 was described as including three regions 62, 64 and 66, but the number of regions included may be any number, as long as the unbendability gently changes between the closely wound region 52 and the second sparsely wound region 46 and the third flexible portion 76 of the flexible tube 26 can be prevented from being bent undesirably or permanently.

Figure 5:
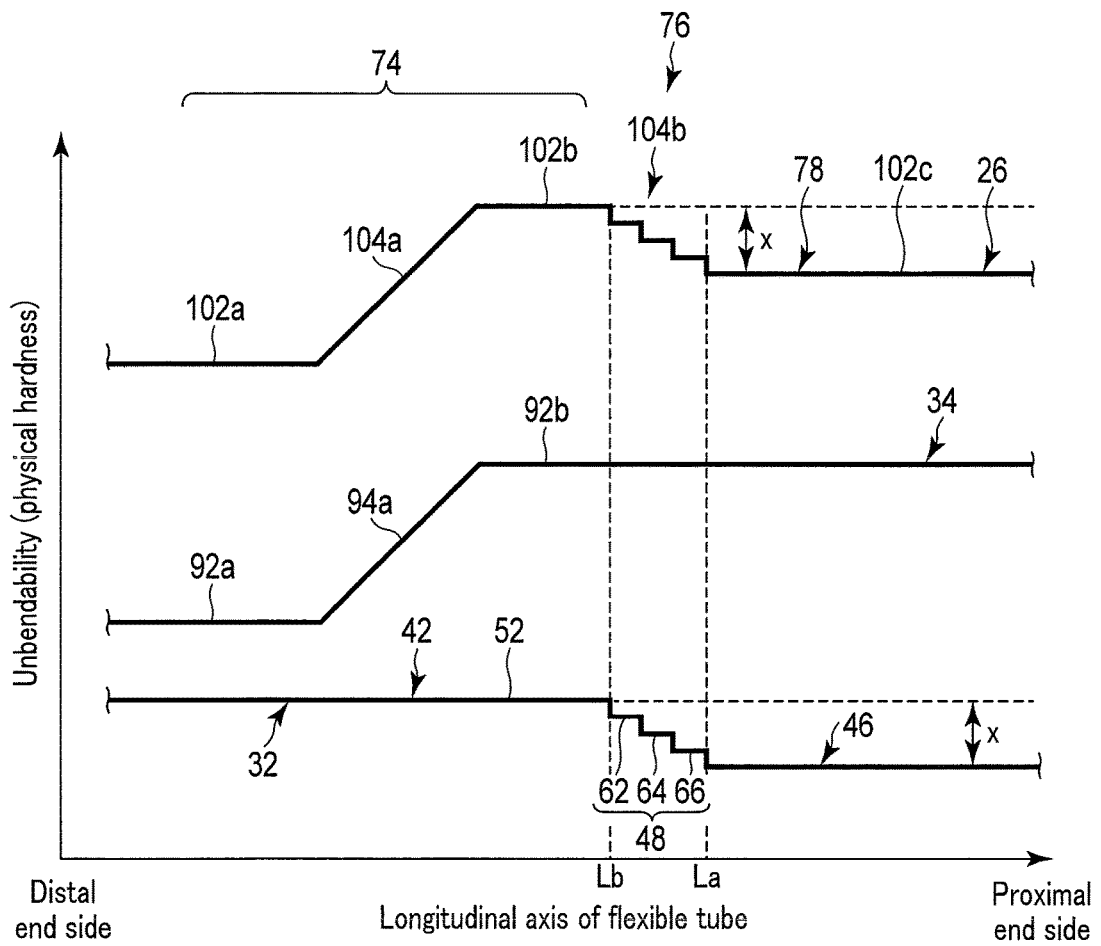
FIG. 5 is a schematic graph illustrating how the flexible tube, helical tube and outer sheath of the insertion section of an insertion apparatus according to the first modification of the first embodiment are hard to bend at positions along the longitudinal axis.

Next, the first modification of the first embodiment will be described with reference to FIG. 5. The first modification is a modification wherein the unbendability and resilience of the outer sheath 34 are adjusted depending upon positions along the longitudinal axis L. In FIG. 5, only that portion of the second flexible portion 74 of the flexible tube 26 which is near the proximal end is shown.

As shown in FIG. 5, the unbendability and resilience of the outer sheath 34 are not constant from the distal end to the proximal end. To be specific, the outer sheath 34 includes, from the distal end to the proximal end, a first constant region 92a in which the unbendability and the resilience are constant, a first change region 94a in which they change, and a second constant region 92b in which they are constant. The first change region 94a is located on the distal end side of the position which is away from the distal end of the outer sheath 34 by length Lb. Therefore, the distal end of the second constant region 92b is located on the distal end side of the position which is away from the distal end of the outer sheath 34 by length Lb. Although the unbendability and the resilience change locally (partially), these changes are changes in one outer sheath 34.

The outer sheath 34 includes a portion covering the outer circumference of the first sparsely wound region 44 (FIGS. 2 and 3) of the helical tube 32 and a portion covering most positions (from the distal end to the proximal end) of the closely wound region 42 of the helical tube 32. These portions form the first constant region 92a where the unbendability and the resilience are constant. The first change region 94a is located on the proximal end side of the first constant region 92a of the outer sheath 34. In the first change region 94a, the unbendability and resilience are higher than those of the first constant region 92a and increase along the longitudinal axis L toward the proximal end. In the first change region 94a of the outer sheath 34, the slope (the amount of change of the hardness) can be properly determined. The slope in the first change region 94a of the outer sheath 34 may be linear or may be a curve expressed by a quadratic function. In either case, the unbendability (physical hardness) should desirably increase from the distal side to the proximal side. The second change region 92b is located on the proximal end side of the first change region 94a of the outer sheath 34. In the second constant region 92b, the unbendability and resilience at the proximal end of the first change region 94a are maintained.

The first constant region 92a is arranged on the outer circumference of the closely wound portion 52 of the closely wound region 42, and forms a first constant flexible region 102a in cooperation with the closely wound region 42. The first change region 94a is arranged on the outer circumference of the closely wound portion 52 of the closely wound region 42, and forms a first flexible change region 104a in cooperation with the closely wound region 42. The second constant region 92b is arranged on the outer circumference of the proximal end portion of the closely wound portion 52 of the closely wound region 42, and forms a second constant flexible region 102b in cooperation with the closely wound region 42. The second constant region 92b is arranged on the outer circumference of the resilience change region 48, and forms a second flexible change region 104b in cooperation with the resilience change region 48. The second constant region 92b is arranged on the outer circumference of the second sparsely wound region 46 of the closely wound region 42, and forms a third constant flexible region 102c in cooperation with the second sparsely wound region 46. In other words, the second constant region 92b cooperates with the outer sheath 34 and forms, from the distal side to the proximal side, the second constant flexible region 102b, the second flexible change region 104b and the third constant flexible region 102c.

It should be noted here that in the helical tube 32 and the outer sheath 34, the difference x between the unbendability of the closely wound portion 52 of the closely wound region 42 of the helical tube 32 and the unbendability of the second sparsely wound region 46 is the difference x between the unbendability of the second constant flexible region 102b of the flexible tube 26 and the unbendability of the third constant flexible region 102c.

In the second constant flexible region 102b, second flexible change region 104b and third constant flexible region 102c, however, the unbendability does not change greatly from the distal side to the proximal side. Because of the second flexible change region 104b, the unbendability is made to decrease gradually. For this reason, the second flexible portion 74 and the third flexible portion 76 of the flexible tube 26 are formed to gently change the flexibility, and do not include any portion where the flexibility changes greatly. Since the flexibility of the flexible tube 26 changes gently, the flexible tube 26 is prevented from being bent undesirably or permanently even if the flexible tube 26 is pushed in to move the distal end portion 12a of the insertion section 12 to a deep portion of the large intestine. The force applied from the third flexible portion 76 and/or the fourth flexible portion 78 can be reliably transmitted to the distal end 26a of the first flexible portion 72. That is, the force which the user applies when the flexible tube 26 is pushed along the longitudinal axis L is reliably transmitted to the distal end 26a of the first flexible portion 72 of the flexible tube 26.

Next, the second modification of the first embodiment will be described with reference to FIG. 6. The second modification is a modification wherein the unbendability and resilience of the outer sheath 34 are adjusted depending upon positions along the longitudinal axis L. The second modification is a further modification of the first modification.

Figure 6:
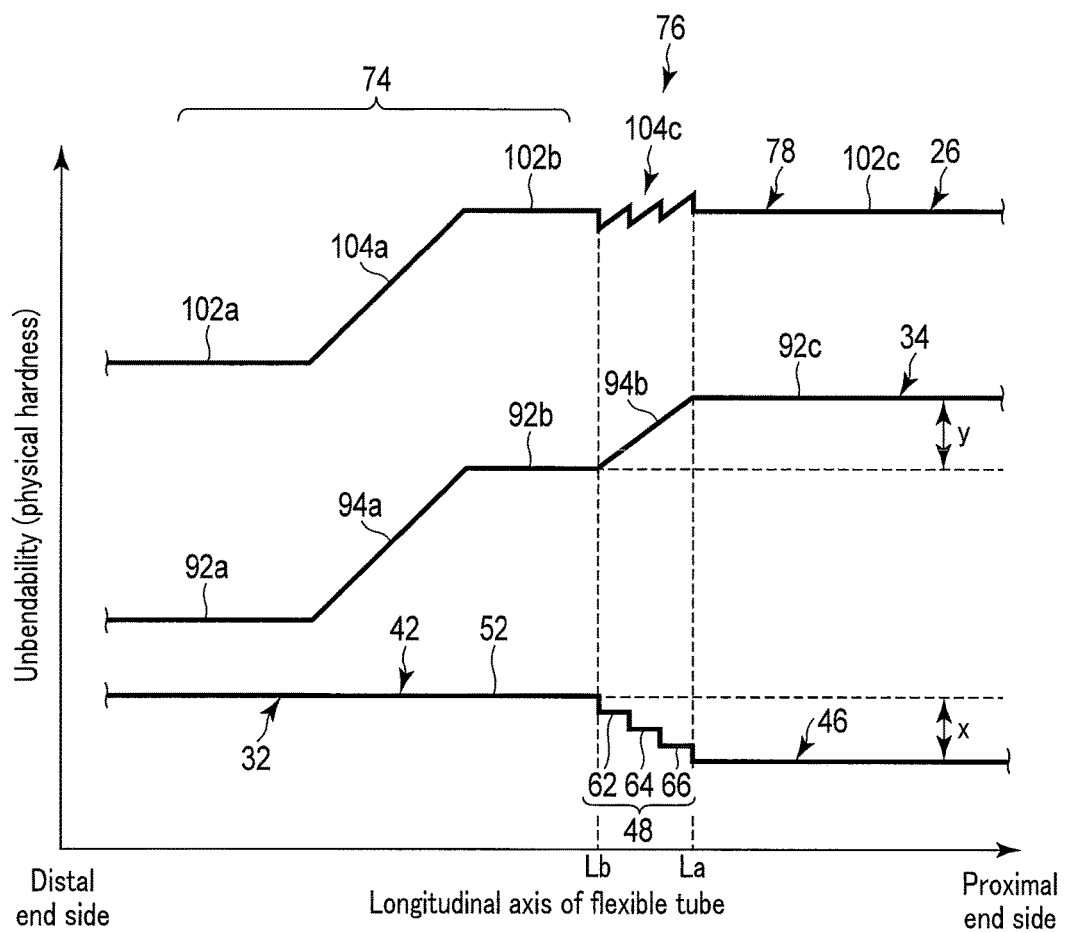
FIG. 6 is a schematic graph illustrating how the flexible tube, helical tube and outer sheath of the insertion section of an insertion apparatus according to the second modification of the first embodiment are hard to bend at positions along the longitudinal axis.

As shown in FIG. 6, the unbendability and resilience of the outer sheath 34 are not constant from the distal end to the proximal end. To be specific, the outer sheath 34 includes, from the distal end to the proximal end, a first constant region 92a in which the unbendability and the resilience are constant, a first change region 94a in which they change, a second constant region 92b in which they are constant, and a third constant region 92c in which they are constant. Compared with the first modification shown in FIG. 5, the second modification is featured in that the second constant region 92b of the outer sheath 34 is short and in that the second change region 94b and the third constant region 92c are located on the proximal end side of the second constant region 92b.

The second change region 94b is located on the proximal side of the second constant region 92b of the outer sheath 34. In the second change region 94b, the unbendability and resilience increase toward the proximal end. In the second change region 94b, the slope can be properly determined. The slope in the second change region 94b of the outer sheath 34 may be linear or a curve expressed by a quadratic function. In either case, the unbendability (physical hardness) should desirably increase from the distal side to the proximal side. The third change region 92c is located on the proximal end side of the second change region 94b of the outer sheath 34. In the third constant region 92c, the unbendability and resilience at the proximal end of the second change region 94b are maintained.

It should be noted here that in the helical tube 32 and the outer sheath 34, the difference x between the unbendability of the closely wound portion 52 of the closely wound region 42 of the helical tube 32 and the unbendability of the second sparsely wound region 46 is substantially equal to the difference y between the unbendability of the second constant region 92b of the outer sheath 34 and the unbendability of the third constant region 92c.

The second constant region 92b of the outer sheath 34 is arranged on the outer circumference of the proximal end portion of the closely wound portion 52 of the closely wound region 42, and forms a second constant flexible region 102b in cooperation with the closely wound region 42. The second change region 94b is arranged on the outer circumference of the resilience change region 48, and forms a second flexible change region 104b in cooperation with the resilience change region 48. Desirably, the distal end of the second change region 94b should be at the position away from the distal end of the outer sheath 34 by length Lb. Desirably, the proximal end of the second change region 94b should be at the position away from the distal end of the outer sheath 34 by length La. Accordingly, the length of the second change region 94b should be preferably equal to the length of the change region 48. The third constant region 92c is arranged on the outer circumference of the second sparsely wound portion 46, and forms a third constant flexible region 102c in cooperation with the second sparsely wound region 46.

It should be noted here that unbendability differences x and y are substantially equal to each other. Because the second change region 94b is provided, the unbendability at the distal end of the second flexible change region 104c and the unbendability at the proximal end of the second flexible change region 104c are substantially equal to each other. Between the distal and proximal ends, the second flexible change region 104c include a portion where the unbendability is higher than those at the distal and proximal ends and a portion where the unbendability is lower than those at the distal and proximal ends. The difference between the unbendability of the high-unbendability portion and the unbendability of the low-unbendability portion is as small as possible. As described above, the second constant flexible region 102b, second flexible change region 104b and third constant flexible region 102c are formed such that the unbendability does not change greatly. For this reason, the second flexible portion 74 and the third flexible portion 76 of the flexible tube 26 are formed to gently change the flexibility, and do not include any portion where the flexibility changes greatly. Since the flexibility of the flexible tube 26 changes gently, the flexible tube 26 is prevented from being bent undesirably or permanently even if the flexible tube 26 is pushed in to move the distal end portion 12a of the insertion section 12 to a deep portion of the large intestine. The force applied from the third flexible portion 76 and/or the fourth flexible portion 78 can be reliably transmitted to the distal end 26a of the first flexible portion 72. That is, the force which the user applies when the flexible tube 26 is pushed along the longitudinal axis L is reliably transmitted to the distal end 26a of the first flexible portion 72 of the flexible tube 26.

Next, the third modification of the first embodiment will be described with reference to FIGS. 7-9. The third modification is a modification wherein the change region 48 of the helical tube 32 is modified.

Figure 7:
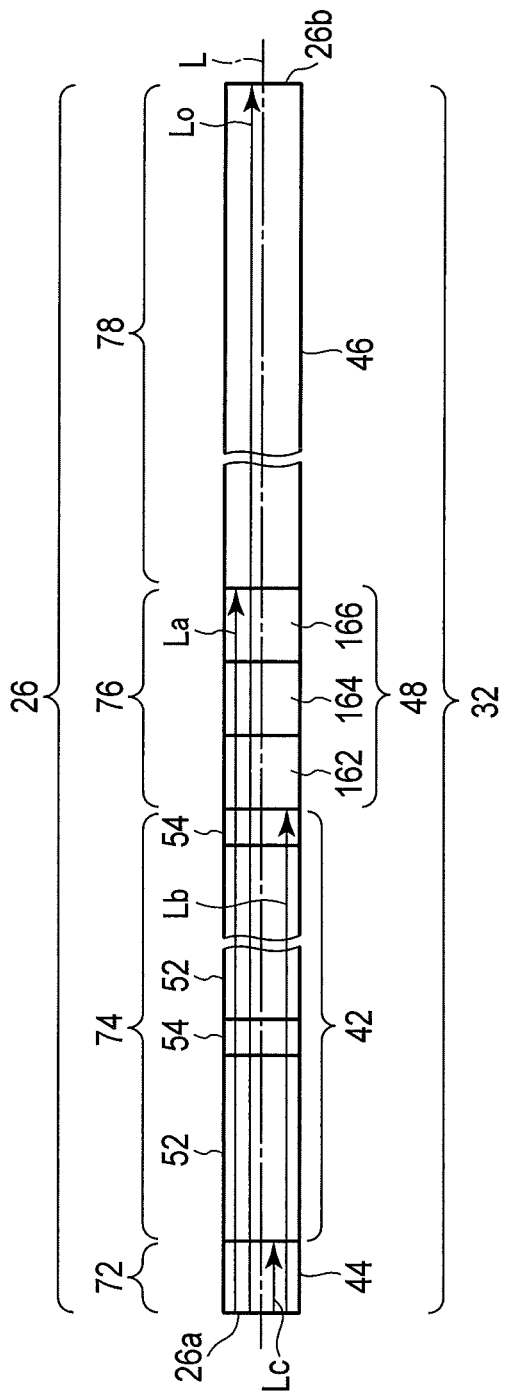
FIG. 7 is a schematic view showing a flexible tube of an insertion section of an insertion apparatus according to the third modification of the first embodiment.
Figure 8:
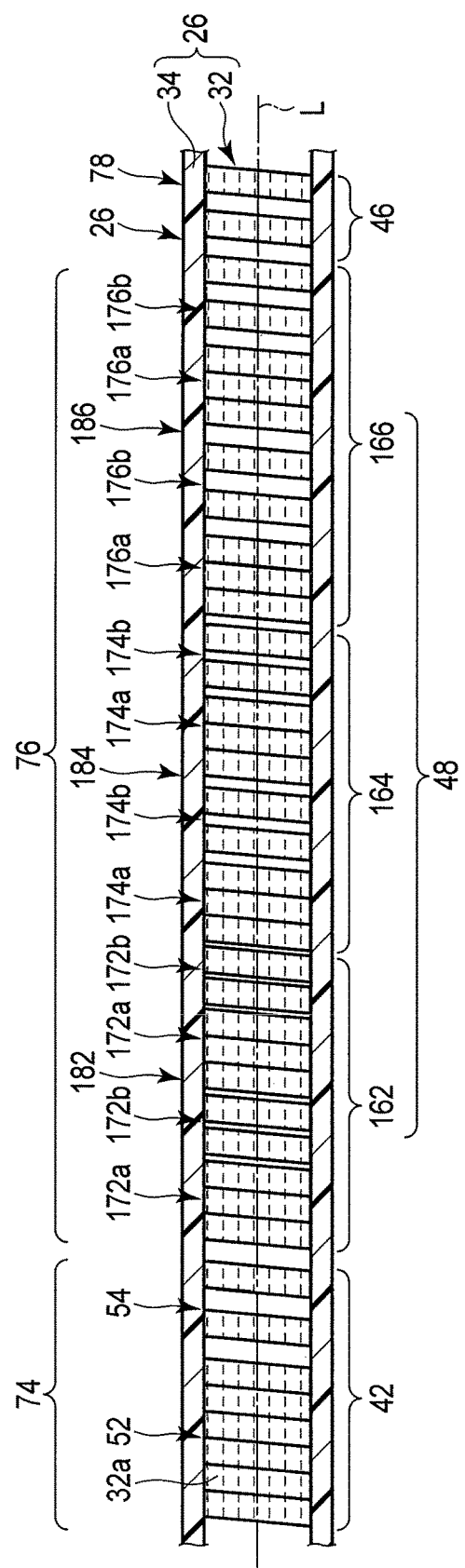
FIG. 8 is a schematic longitudinal section illustrating part of the flexible tube of the insertion section of the insertion apparatus according to the third modification of the first embodiment.
Figure 9:
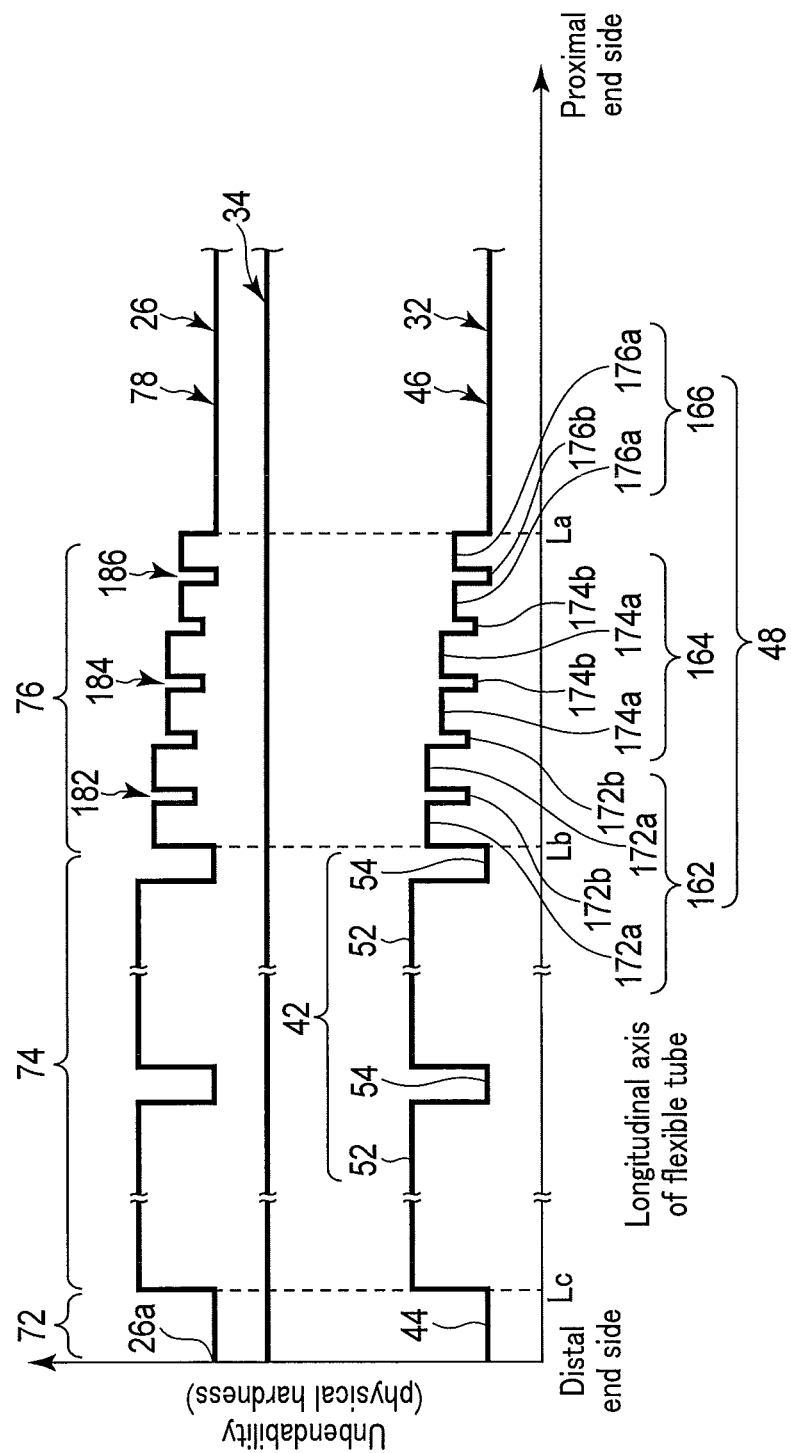
FIG. 9 is a schematic graph illustrating how the flexible tube, helical tube and outer sheath of the insertion section of the insertion apparatus according to the third modification of the first embodiment are hard to bend at positions along the longitudinal axis.

As shown in FIGS. 7 and 8, the closely wound region 42 according to the modification includes a sparsely wound portion 54 at the proximal end thereof. This means that the proximal end of the closely wound region 42 of the first embodiment may be a closely wound portion 52 or a sparsely wound portion 54.

As shown in FIG. 8, the change region 48 of the present modification includes a first region 162, a second region 164 and a third region 166 from the distal side to the proximal side along the longitudinal axis L. The first region (maintaining region) 162, the second region (maintaining region) 164 and the third region (maintaining region) 166 are regions in which respective unbendabilityes and resiliences are maintained constant. The unbendability and resilience of the flexible tube 26 are decreased along the longitudinal axis L in a direction away from a position in the neighborhood of the closely wound region 42. The change region 48 of the present modification includes a plurality of maintaining regions 162, 164 and 166 in which respective unbendabilityes and resiliences are maintained constant. The change region 48 decreases the resilience stepwise along the longitudinal axis L in a direction away from a position in the neighborhood of the closely wound region 42.

The first region 162 includes a first short closely wound portion (first closely wound portion) 172a in which the adjacent wire portions 32a are applied with a tight contact force based on an initial tensile force and a first short sparsely wound portion (first sparsely wound portion) 172b in which the adjacent wire portions 32a are separate from each other. The first short closely wound portion 172a and the first short sparsely wound portion 172b are alternately arranged. In the first short closely wound portion 172a, the tight contact force of the wire portions 32a is decreased from that of the closely wound portion 52 of the closely wound region 42. The first short closely wound portion 172a is shorter than the closely wound portion 52 along the longitudinal axis L. For example, it is desirable that each first short closely wound portion (first closely wound portion) 172a have a length corresponding to several turns. The intervals of the adjacent wire portions 32a of the first short sparsely wound portion 172b are shorter than those of the wire portions 32a of the sparsely wound portion 54 of the closely wound region 42. With this structure, the first short sparsely wound portion 172b has a higher unbendability and a higher resilience than those of the sparsely wound portion 54. The first short sparsely wound portion 172b is substantially as long as, or shorter than the closely wound portion 54 along the longitudinal axis L. For example, it is desirable that each first short sparsely wound portion (first sparsely wound portion) 172b have a length corresponding to several turns. It is preferable that the total length of the first short closely wound portion 172a and the first short sparsely wound portion 172b be less than the length of one closely wound portion 52 of the closely wound region 42.

The second region 164 includes a second short closely wound portion (second closely wound portion) 174a in which the adjacent wire portions 32a are applied with a tight contact force based on an initial tensile force and a second short sparsely wound portion (second sparsely wound portion) 174b in which the adjacent wire portions 32a are separate from each other. The second short closely wound portion 174a and the second short sparsely wound portion 174b are alternately arranged. In the second short closely wound portion 174a, the tight contact force of the wire portions 32a is decreased from that of the first short closely wound portion 172a. The second short closely wound portion 174a is shorter than the closely wound portion 52 along the longitudinal axis L. For example, it is desirable that each second short closely wound portion (second closely wound portion) 174a have a length corresponding to several turns. The intervals of the adjacent wire portions 32a of the second short sparsely wound portion 174b are shorter than those of the wire portions 32a of the sparsely wound portion 54 and are longer than those of the wire portions 32a of the first short sparsely wound portion 172b. With this structure, the second short sparsely wound portion 172b has a lower unbendability and a lower resilience than those of the first short sparsely wound portion 172b and has a higher unbendability and a higher resilience than those of the sparsely wound portion 54. The second short sparsely wound portion 174b is substantially as long as, or shorter than the sparsely wound portion 54 along the longitudinal axis L. For example, it is desirable that each second short sparsely wound portion (second sparsely wound portion) 174b have a length corresponding to several turns.

The third region 166 includes a third short closely wound portion 176a in which the adjacent wire portions 32a are applied with a tight contact force based on an initial tensile force and a third short sparsely wound portion 176b in which the adjacent wire portions 32a are separate from each other. The third short closely wound portion 176a and the third short sparsely wound portion 176b are alternately arranged. In the third short closely wound portion 176a, the tight contact force of the wire portions 32a is decreased from those of the first short closely wound portion 172a and the second short closely wound portion 174a. The third short closely wound portion 176a is shorter than the closely wound portion 52 along the longitudinal axis L. For example, it is desirable that each third short closely wound portion (third closely wound portion) 176a have a length corresponding to several turns. The intervals of the adjacent wire portions 32a of the third short sparsely wound portion 176b are slightly shorter than those of the wire portions 32a of the sparsely wound portion 54 and are longer than those of the wire portions 32a of the second short sparsely wound portion 174b. With this structure, the third short sparsely wound portion 176b has a lower unbendability and a lower resilience than those of the second short sparsely wound portion 174b and has a higher unbendability and a higher resilience than those of the sparsely wound portion 54 and second sparsely wound region 46. The third short sparsely wound portion 176b is substantially as long as, or shorter than the sparsely wound portion 54 along the longitudinal axis L. For example, it is desirable that each third short sparsely wound portion (third sparsely wound portion) 176b have a length corresponding to several turns.

As described above, the change region 48 includes: a first short closely wound portion (first closely wound portion) 172a arranged at a position adjacent to the closely wound region 42; a second short closely wound portion (second closely wound portion) 174a arranged at a position adjacent to the first short closely wound portion 172a and separate from the closely wound region 42 and having a tight contact force equal to or lower than the tight contact force of the wire portions 32a of the first short closely wound portion 172a; and a first sparsely wound portion 172b arranged between the first and second short closely wound portions (first and second closely wound portions) 172a and 174a and having a higher resilience than the second sparsely wound region 46. The total length of the first short closely wound portion 172a and the first short sparsely wound portion 172b is less than the length of the closely wound portion 52 of the closely wound region 42.

Where the longitudinal axis L of the first to third closely wound portions 172a, 174a and 176a is vertical, the first to third closely wound portions 172a, 174a and 176a maintain the state where the wire portions 32a of the closely wound portions 172a, 174a and 176a are in tight contact with each other, against the force of gravity, and no gap is provided between the wire portions 32a.

In the present modification, it is assumed that the unbendability and resilience of the outer sheath 34 are constant from the distal end to the proximal end. As described above, roughly speaking, the unbendability and resilience of the third flexible portion 76 can be regarded as the respective sums of the unbendability and resilience of the change region 48 of the helical tube 32 and the unbendability and resilience of the outer sheath 34 (the change region 48 is located on the longitudinal axis L and radially inward, and the outer sheath 34 is located radially outward).

The third flexible portion 76 includes, from the distal side to the proximal side, a first portion (maintaining region) 182 which is easier to bend than the closely wound portion 52 covered with the outer sheath 34 and maintains a proper unbendability, a second portion (maintaining region) 184 which is easier to bend than the first portion 184 and maintains a proper unbendability, and a third portion (maintaining region) 186 which is easier to bend than the second portion 184 and maintains a proper unbendability.

The unbendability and resilience of the third flexible portion 76 are substantially constant at positions where the first region 162 of the helical tube 32 is covered with the outer sheath 34. The unbendability and resilience of the third flexible portion 76 are substantially constant at positions where the second region 164 of the helical tube 32 is covered with the outer sheath 34. The unbendability and resilience of the third flexible portion 76 are substantially constant at positions where the third region 166 of the helical tube 32 is covered with the outer sheath 34. The unbendability and resilience of the third flexible portion 76 decrease stepwise from the distal end to the proximal end at positions where the outer sheath 34 is provided on the change region 48 of the helical tube 32.

As can be seen, the unbendability of the distal end portion of the third flexible portion 76 is made close to the unbendability of the proximal end portion of the second flexible portion 74, and the unbendability of the proximal end portion of the third flexible portion 76 is made close to the unbendability of the distal end portion of the fourth flexible portion 78. In particular, in the third flexible portion 76, the unbendability is gradually decreased, from the distal side to the proximal side along the longitudinal direction L, from that of the second flexible portion 74 toward that of the fourth flexible portion 78. With this structure, the unbendability of the third flexible portion 76 decreases stepwise from the distal end to the proximal end. In other words, the third flexible portion 76 is formed such that its bending easiness increases from the distal end to the proximal end. The third flexible portion 76 enables the unbendability to change gently, unlike the case where the fourth flexible portion 78 is arranged directly at the proximal end of the second flexible portion 74. That is, when the user inserts the insertion section 12, namely the flexible tube 26, to a deep portion of the passage, while holding the third flexible portion 76 and/or the fourth flexible portion 78, the third flexible portion 76 between the distal end of the fourth flexible portion 78 and the proximal end of the second flexible portion 74 is prevented from being bent undesirably or permanently, and the distal end portion of the fourth flexible portion 78 is prevented from being bent undesirably or permanently. The present modification can provide a flexible tube 26 which can be easily inserted into a winding passage (e.g., the large intestine) from a partly inserted state, and can also provide an insertion apparatus 10 having such a flexible tube 26.

Next, the fourth modification of the first embodiment will be described with reference to FIG. 10. The fourth modification is a further modification of the first to third modifications, specifically a modification of the outer sheath 34 of the third modification.

Figure 10:
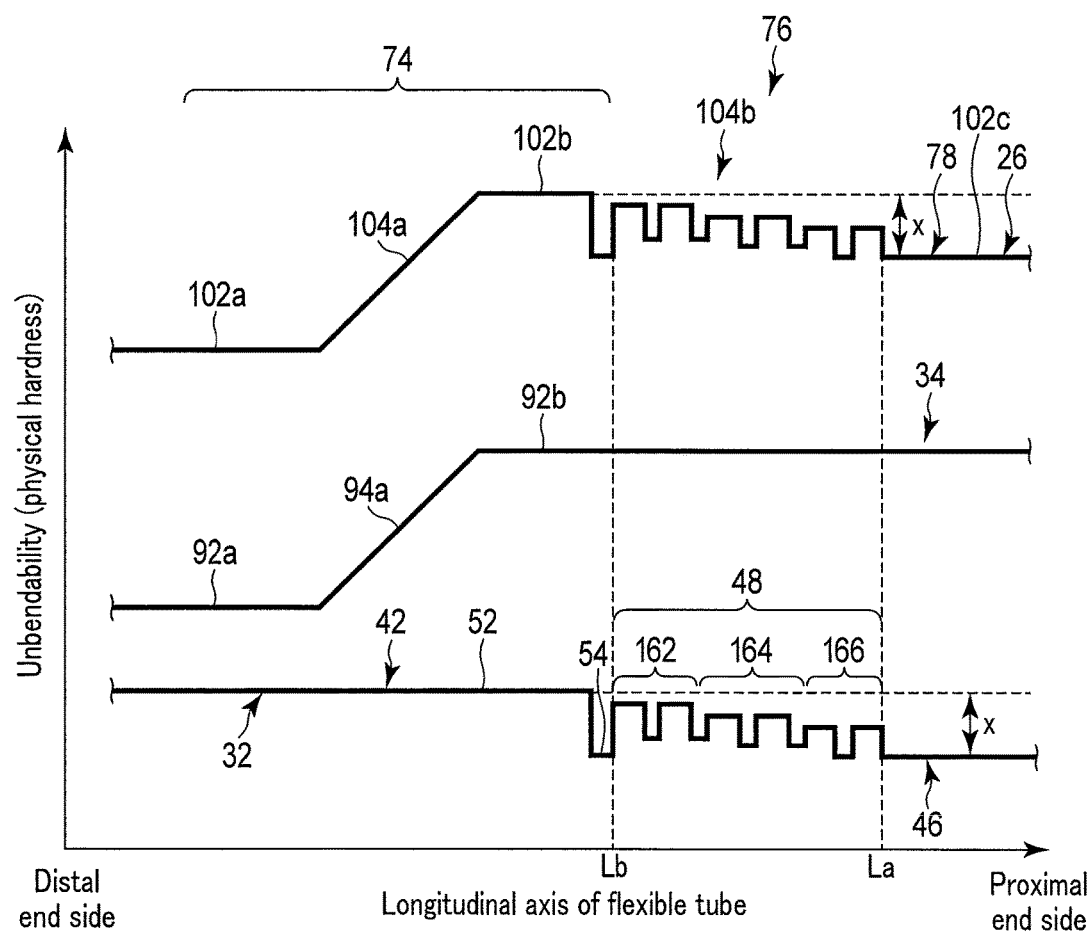
FIG. 10 is a schematic graph illustrating how the flexible tube, helical tube and outer sheath of the insertion section of an insertion apparatus according to the fourth modification of the first embodiment are hard to bend at positions along the longitudinal axis.

As shown in FIG. 10, the outer sheath 34 includes, from the distal end to the proximal end, a first constant region 92a in which the unbendability and the resilience are constant, a first change region 94a in which they change, and a second constant region 92b in which they are constant.

It should be noted here that in the helical tube 32 and the outer sheath 34, the difference x between the unbendability of the closely wound portion 52 of the closely wound region 42 and the unbendability of the second sparsely wound region 46 is the difference x between the unbendability of the second constant flexible region 102*b* of the flexible tube 26 and the unbendability of the third constant flexible region 102*c*.

In the second constant flexible region 102*b*, second flexible change region 104*b* and third constant flexible region 102*c*, however, the unbendability does not decrease greatly but gradually. For this reason, the second flexible portion 74 and the third flexible portion 76 of the flexible tube 26 are formed to gently change the flexibility, and do not include any portion where the flexibility changes greatly. Since the flexibility of the flexible tube 26 changes gently, the flexible tube 26 is prevented from being bent undesirably or permanently even if the flexible tube 26 is pushed in to move the distal end portion 12*a* of the insertion section 12 to a deep portion of the large intestine. The force applied from the third flexible portion 76 and/or the fourth flexible portion 78 can be reliably transmitted to the distal end 26*a* of the first flexible portion 72. That is, the force which the user applies when the flexible tube 26 is pushed along the longitudinal axis L is reliably transmitted to the distal end 26*a* of the first flexible portion 72 of the flexible tube 26.

Next, the fifth modification of the first embodiment will be described with reference to FIG. 11. The fifth modification is a further modification of the first to fourth modifications, specifically a modification of the outer sheaths 34 of the third and fourth modifications.

Figure 11:
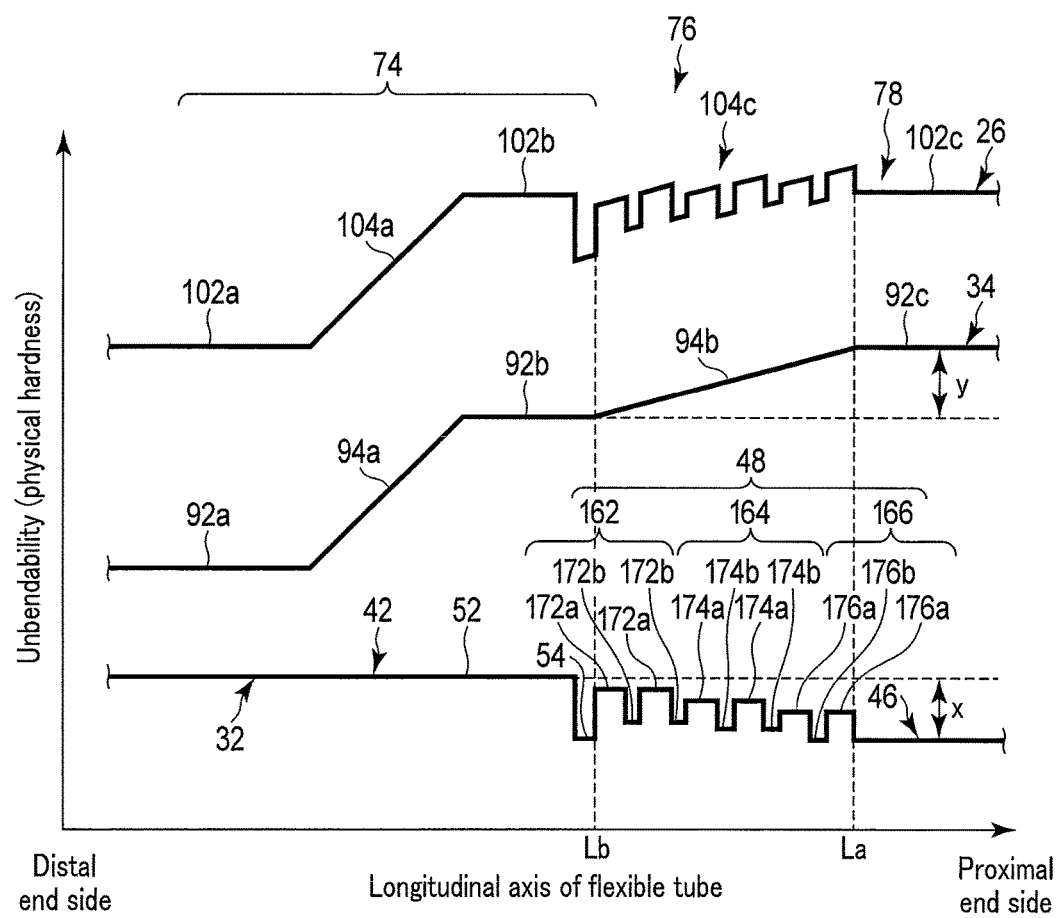
FIG. 11 is a schematic graph illustrating how the flexible tube, helical tube and outer sheath of the insertion section of an insertion apparatus according to the fifth modification of the first embodiment are hard to bend at positions along the longitudinal axis.

As shown in FIG. 11, the outer sheath 34 includes, from the distal end to the proximal end, a first constant region 92*a* in which the unbendability and the resilience are constant, a first change region 94*a* in which they change, a second constant region 92*b* in which they are constant, a second change region 94*b* in which they change, and a third constant region 92*c* in which they are constant. The outer sheath 34 of the fifth modification is similar to that of the second modification shown in FIG. 6. That is, compared with the fourth modification shown in FIG. 10, the fifth modification is featured in that the second constant region 92*b* is short and in that the second change region 94*b* and the third constant region 92*c* are located on the proximal end side of the second constant region 92*b*.

As in the second modification, the helical tube 32 and the outer sheath 34 are formed such that the difference x between the unbendability of the closely wound portion 52 of the closely wound region 42 and the unbendability of the second sparsely wound region 46 is substantially equal to the difference y between the unbendability of the second constant region 92*b* and the unbendability of the third constant region 92*c*. Because the second change region 94*b* is provided, the unbendability at the distal end of the second flexible change region 104*c* and the unbendability at the proximal end of the second flexible change region 104*c* are substantially equal to each other. That is, the outer sheath 34 is formed such that the portion on the outer side of the second sparsely wound region 46 is harder to bend than the portion on the outer side of the closely wound region 42. This structure is intended to compensate for the difference x between the unbendability of the closely wound portion 52 of the closely wound region 42 and the unbendability of the second sparsely wound region 46.

With this structure, the second constant flexible region 102*b*, second flexible change region 104*c* and third constant flexible region 102*c* are formed such that the unbendability and resilience do not change greatly. For this reason, the second flexible portion 74, third flexible portion 76 and fourth flexible portion 78 of the flexible tube 26 do not include any portion where the unbendability and resilience change greatly. Since the flexible tube 26 does not include a portion where the unbendability changes greatly, the flexible tube 26 is prevented from being bent undesirably or permanently even if the flexible tube 26 is pushed in to move the distal end portion 12*a* of the insertion section 12 to a deep portion of the large intestine. The force applied from the fourth flexible portion 78 can be reliably transmitted to the distal end 26*a* of the first flexible portion 72. That is, the force which the user applies when the third flexible portion 76 and/or the fourth flexible portion 78 of the flexible tube 26 is pushed along the longitudinal axis L is reliably transmitted to the distal end 26*a* of the first flexible portion 72 of the flexible tube 26.

Next, the second embodiment will now be described with reference to FIGS. 12 and 13. The second embodiment is a modification of the first embodiment, including all modifications mentioned above. Elements which are the same as those described in connection with the first embodiment or which have the same functions as those described in connection with the first embodiment will be assigned with the same reference symbols, and detailed descriptions of such elements will be omitted.

Figure 12:
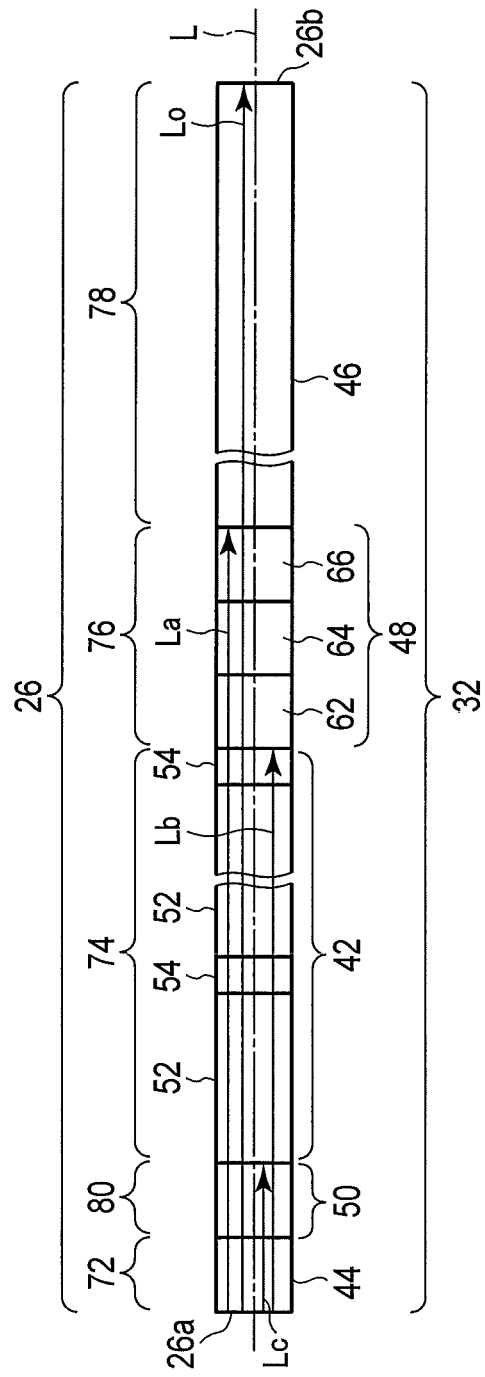
FIG. 12 is a schematic view showing a flexible tube of an insertion section of an insertion apparatus according to the second embodiment.

As shown in FIG. 12, the flexible tube 26 of the second embodiment comprises not only a change region (a proximal-end-side change region) 48 between the closely wound region 42 and the second sparsely wound region 46 but also a change region (a distal-side change region) 50 between the closely wound region 42 and the first sparsely wound region 44.

Since the structure of the proximal-end-side change region 48 was described in connection with the first embodiment (FIGS. 4 to 4B) including its modifications (FIGS. 5 to 11), a repetitive description of the structure will be omitted. In FIG. 2 (illustrating the first embodiment), a structure where the first region 62 is connected directly to the proximal end of the closely wound portion 52 is shown. The first region 62 may be connected directly to the proximal end of the sparsely wound portion 54, as shown in FIG. 12. In other words, the distal end of the proximal-end-side change region 48 of the helical tube 32 may be continuous with the sparsely wound portion 54 or with the closely wound portion 52.

The distal-side change region 50 shown in FIG. 13 has a structure opposite to that of the proximal-side change region 48 from the distal side to the proximal side along the longitudinal axis L. The distal-side change region 50 includes first to third distal-side regions (maintaining regions) 262, 264 and 266.

In the first region 262, the intervals of the adjacent wire portions 32*a* are constant. Likewise, in the second region 264, the intervals of the adjacent wire portions 32*a* are constant. Likewise, in the third region 266, the intervals of the adjacent wire portions 32*a* are constant.

The intervals of the adjacent wire portions 32*a* of the first region 262 are shorter than those of the wire portions 32*a* of the first sparsely wound portion 44. The first region 262 is easier to bend and has a low resilience than the closely wound region 42. In other words, the first region 262 is easier to bend than the closely wound region 42, and is harder to return to the substantially linear state from a bent state than the closely wound region 42.

The intervals of the adjacent wire portions 32*a* of the second region 264 are shorter than those of the adjacent wire portions 32*a* of the first region 262 but are longer than those of the adjacent wire portions 32*a* of the third region 266. The second region 264 is easier to bend and has a lower resilience than the closely wound portion 52 of the closely wound region 42. The second region 264 is harder to bend and has a higher resilience than the sparsely wound portion 54. In addition, the second region 264 is easier to bend than the first region 262.

The intervals of the adjacent wire portions 32a of the third region 266 are shorter than those of the adjacent wire portions 32a of the first and second regions 262 and 264. The third region 266 is easier to bend and has a lower resilience than the closely wound portion 52 of the closely wound region 42. The third region 266 is harder to bend and has a higher resilience than the sparsely wound portion 54. In addition, the third region 266 is harder to bend and has a higher resilience than the first and second regions 262 and 264.

The change region 50 of the helical tube 32 of the present embodiment includes a plurality of maintaining regions 266, 264 and 262 in which respective unbendabilityes and resiliences are maintained constant. The change region 50 decreases the unbendability and the resilience stepwise along the longitudinal axis L in a direction away from a position in the neighborhood of the closely wound region 42.

As described above, the distal-side change region 50 of the helical tube 32 is configured such that the unbendability and resilience of the distal end portion (i.e., a position close to the first sparsely wound region 44) are set to be close to those of the first sparsely wound region 44 and the unbendability and resilience of the proximal end portion (i.e., a portion close to the closely wound region 42) are set to be close to those of the closely wound region 42. In other words, the distal-side change region 50 increases the resilience of the first sparsely wound region 44 stepwise from the distal end to the proximal end along the longitudinal axis L, such that the increased resilience becomes closer to the resilience of the closely wound portion 52 of the closely wound region 42.

The distal-side change region 50 and the outer sheath 34 on the outer side of the change region 50 cooperate with each other, and a fifth flexible portion 80 is formed thereby. The fifth flexible portion 80 is formed between the first and second flexible portions 72 and 74 described in connection with the first embodiment. Roughly speaking, the unbendability of the fifth flexible portion 80 can be regarded as the sum of the unbendability of the distal-side change region 50 and the unbendability of the outer sheath 34 (the change region 50 is located on the longitudinal axis L and radially inward, and the outer sheath 34 is located radially outward). Roughly speaking, the resilience of the fifth flexible portion 80 can be regarded as the sum of the resilience of the change region 50 of the helical tube 32 and the resilience of the outer sheath 34 (the change region 50 is located on the longitudinal axis L and radially inward, and the outer sheath 34 is located radially outward). From a microscopic point of view, the unbendability and resilience of the fifth flexible portion 80 vary depending upon positions, i.e., a position where the first region 262 is provided, a position where the second region 264 is provided, and a position where the third region 266 is provided. With this structure, the unbendability and resilience of the fifth flexible portion 80 increase stepwise from the distal end to the proximal end. From a macroscopic point of view, the unbendability and resilience of the fifth flexible portion 80 increase substantially linearly from the distal end to the proximal end, because the outer sheath 34 is provided on the change region 50.

The first sparsely wound region 44 of the helical tube 32 has a resilience lower than that of the change region 50. For this reason, the first flexible portion 72 is easier to bend than the fifth flexible portion 80. On the other hand, the closely wound portion 52 of the closely wound region 42 is harder to bend and has a higher resilience than the change region 50. For this reason, the fifth flexible portion 80 is easier to bend than the second flexible portion 74.

The fifth flexible portion 80 includes, from the distal side to the proximal side, a first portion 282a which is harder to bend than the first flexible portion 72, a second portion 282b which is harder to bend than the first portion 282a, and a third portion 282c which is harder to bend than the second portion 282b. In the first portion (maintaining region) 282a, second portion (maintaining region) 282b and third portion (maintaining region) 282c of the fifth flexible portion 80, the respective unbendabilityes are maintained.

In the fifth flexible portion 80, the unbendability changes at the first change portion 284a (which is the border between the distal side of the first portion 282a and the proximal end of the first flexible portion 72), at the second change portion 284b (which is the border between the first portion 282a and the second portion 282b), at the third change portion 284c (which is the border between the second portion 282b and the third portion 282c) and at the fourth change portion 284d (which is the border between the third portion 282c and the distal end of the second flexible portion 74).

The resilience difference between the first sparsely wound region 44 and the first portion 282a of the change region 50 occurs in the first change portion 284a. The resilience difference between the first portion 282a of the change region 50 and the second portion 282b occurs in the second change portion 284b. The resilience difference between the second portion 282b of the change region 50 and the third portion 282c occurs in the third change portion 284c. The resilience difference between the third portion 282c of the change region 50 and the closely wound portion 52 of the closely wound region 42 occurs in the fourth change portion 284d.

As can be seen, the unbendability of the distal end portion of the fifth flexible portion 80 is made close to the unbendability of the proximal end portion of the first flexible portion 72, and the unbendability of the proximal end portion of the fifth flexible portion 80 is made close to the unbendability of the distal end portion of the second flexible portion 74. In particular, the unbendability of the fifth flexible portion 80 is changed at the borders (the first to fourth change portions 284a, 284b, 284c and 284d) stepwise. With this structure, the unbendability of the fifth flexible portion 80 increases stepwise from the distal side to the proximal side. A description will be given of how the insertion apparatus 10 of the present embodiment operates. In the description below, the large intestine will be referred to as the passage into which the insertion section 12 of the insertion apparatus 10 is inserted.

The user of the insertion apparatus 10 holds the second flexible portion 74 or the third flexible portion 76 of the flexible tube 26. Then, the user inserts the distal-end hard portion 22, the bending portion 24 and the flexible tube 26 of the insertion section 12 in this order into a narrow and curved passage (from the anus into the curved large intestine). The user changes the held positions of the flexible tube 26 gradually toward the proximal end, thereby permitting the distal end portion 12a of the insertion section 12 to be inserted into the passage.

The unbendability and the resilience of the fifth flexible portion 80 increase stepwise from the distal end of the fifth flexible portion 80 to the distal end of the second flexible portion 74 such that the unbendability and the resilience become closer to those of the second flexible portion 74.

The fifth flexible portion 80 is harder to bend than the first flexible portion 72 but is easier to bend than the second bending portion 74. The unbendability of the fifth flexible portion 80 is determined such that the fifth flexible portion 80 can be bent when an external force is applied by the inner circumference (inner wall) of the curved portion of the large intestine. Because of the fifth flexible portion 80 arranged between the first and second flexible portions 72 and 74, the unbendability is made to change gently between the first flexible portion 72 and the second flexible portion 74.

For example, when the distal end portion 12a of the insertion section 12 is inserted from the anus to a deep portion of the large intestine, the first flexible portion 72 is bent along the inner circumferential surface of the passage. The second flexible portion 74 of the fifth flexible portion 80 is also bent by the external force applied from the inner circumferential surface of the passage and exceeding the unbendability. Thus, the insertion section 12, including the first flexible portion 72, fifth flexible portion 80 and second flexible portion 74, bends along the curve of the flexible passage (the large intestine).

The resilience exhibited by the fifth flexible portion 80 is higher than that of the first flexible portion 72 but is lower than that of the second flexible portion 74. For this reason, the fifth flexible portion 80 serves to make the curve of the large intestine substantially linear when the fifth flexible portion 80 is bent. Because of this resilience, the fifth flexible portion 80 can return to the substantially linear state from a bent state. After the first flexible portion 72 passes a curve of the passage, the fifth flexible portion 80 makes the curve of the passage substantially linear by utilization of the resilience of the fifth flexible portion 80 and the resilience of the second flexible portion 74. After the fifth flexible portion 80 and the second flexible portion 74 are bent, the insertion section 12 is pulled back a little such that the external force applied to the fifth flexible portion 80 and the second flexible portion 74 is reduced. In this manner, the fifth flexible portion 80 and the second flexible portion 74 are allowed to easily show their resilience. Because of this, a passage having a small radius of curvature, such as the sigmoid colon, can be made substantially linear. Since the first flexible portion 72 is also resilient, it returns to a substantially linear state. In this manner, the distal end portion 12a of the insertion section 12 can be inserted up to a deep portion of the passage.

After the first flexible portion 72, the fifth flexible portion 80 and second flexible portions 74 are sequentially bent and pass the curve of the passage, the passage is made substantially linear by utilization of the resilience of the fifth flexible portion 80 and the resilience of the second flexible portion 74. By doing so, a so-called stick phenomenon is prevented, in which the inner wall of the large intestine gets stuck with the distal end portion 12a of the insertion section 12 or the distal end 26a of the flexible tube 26.

In this manner, the first flexible portion 72, fifth flexible portion 80 and second flexible portion 74 of the flexible tube 26 of the insertion section 12 are properly bent in response to the external force applied from the inner circumferential surface of the passage, and the passage is made substantially linear by utilization of the fifth flexible portion 80 and the resilience of the second flexible portion 74. By repeatedly performing these operations, the distal end portion 12a of the insertion section 12 is made to move to a deep portion of the passage.

The fifth flexible portion 80 serves to adjust the bending easiness such that the bending easiness changes gently between the distal end of the second flexible portion 74 and the proximal end of the first flexible portion 72. When the user inserts the distal end portion 12a of the insertion section 12 to a deep portion of the passage, while holding the third flexible portion 76 and/or the fourth flexible portion 78, the force applied by the user can be easily transmitted to the first flexible portion 72 i.e., to the distal end 26a of the flexible tube 26, by way of the third flexible portion 76, second flexible portion 74 and fifth flexible portion 80.

That is, when the user inserts the insertion section 12, namely the flexible tube 26, to a deep portion of the passage, while holding the third flexible portion 76 and/or the fourth flexible portion 78, the third flexible portion 76 between the distal end of the fourth flexible portion 78 and the proximal end of the second flexible portion 74 and the distal end portion of the fourth flexible portion 78 are prevented from being bent undesirably or permanently. In addition, the fifth flexible portion 80 is prevented from being bent undesirably or permanently. In other words, the force which the user applies when the third flexible portion 76 and/or the fourth flexible portion 78 of the flexible tube 26 is pushed along the longitudinal axis L is reliably transmitted to the distal end 26a of the first flexible portion 72 by way of the third flexible portion 76, second flexible portion 74 and fifth flexible portion 80.

Since the third flexible portion 76 is arranged between the second flexible portion 74 and the fourth flexible portion 78 and the fifth flexible portion 80 is arranged between the first flexible portion 72 and the second flexible portion 74, an advancing force applied along the longitudinal axis L from any position on the proximal side of the proximal end of the second flexible portion 74 of the flexible tube 26 can be easily transmitted to the second flexible portion. Further, the fifth flexible portion 80 enables the force to be easily transmitted from the second flexible portion 74 to the first flexible portion 72. Therefore, the amount of operation at the third flexible portion 76 and/or fourth flexible portion 78 held by the right hand of the user of the insertion apparatus 10 is easily transmitted to the distal end 26a of the flexible tube 26 (namely, the distal end of the first flexible portion 72), and the flexible tube 26 can be easily inserted into a deep portion of the passage. That is, the distal end portion 12a of the insertion section 12 can be easily inserted to a deep portion of the passage.

As described above, the insertion apparatus 10 of the present embodiment has the following features:

The change region 50 is arranged between the proximal end of the first sparsely wound region 44 of the helical tube 32 and the distal end of the closely wound portion 52 of the closely wound region 42, such that the unbendability and resilience of the helical tube 32 increase stepwise from the distal side to the proximal side. The outer circumference of the helical tube 32 is covered with the outer sheath 34 having a constant unbendability and a constant resilience, and the unbendability and the resilience are made to change gently and stepwise between the first flexible portion 72 and the fifth flexible portion 80. In addition, the unbendability and the resilience are made to change gently and stepwise between the fifth flexible portion 80 and the second flexible portion 74.

Since the fifth flexible portion 80 and the second flexible portion 74 are arranged on the distal end side of the flexible tube 26, desirable bending characteristics and desirable resilience are exhibited in response to an external force. Therefore, the flexible tube 26 of the insertion section 12 bends in accordance with a curve of the flexible passage, such as the large intestine. After the fifth flexible portion 80 and the second flexible portion 74 pass the curve of the passage, the curve of the passage is made substantially linear by utilization of the resilience of the flexible tube 26 (the property of returning to the original linear state from the bent state), and the insertion section 12 can be inserted further into the passage. As described above, the flexible tube 26 of the present embodiment can easily make the passage substantially linear, as compared with a flexible tube having low resilience.

Since the unbendability of the portion between the second flexible portion 74 and the fourth flexible portion 78 is adjusted by the third flexible portion 76, and the unbendability of the portion between the first flexible portion 72 and the second flexible portion 74 is adjusted by the fifth flexible portion 80, the pushing force with which the flexible tube 26 is inserted into the passage can be easily transmitted from the third flexible portion 76 and/or the fourth flexible portion 78 to the distal end 26a of the first flexible portion 72.

The present embodiment can provide a flexible tube 26 which can be easily inserted into a deep portion of a passage, and can also provide an insertion apparatus 10 having such a flexible tube 26.

Next, the first modification of the second embodiment will be described with reference to FIG. 14.

As shown in FIG. 14, the change region 50 of the helical tube 32 has a structure opposite to that of the change region 48 shown in FIG. 8 (i.e., the change region of the third modification of the first embodiment). The change region 50 shown in FIG. 14 has a structure opposite to that of the change region 48 shown in FIG. 8 from the distal side to the proximal side along the longitudinal axis L. The change region 50 includes a first region (maintaining region) 362 and a second region (maintaining region) 164, which are continuous from the distal end to the proximal end (from a position far from the closely wound region 42 to a position close to the closely wound region 42) along the longitudinal axis L.

The first region 362 includes a first short sparsely wound portion 372a in which the adjacent wire portions 32a are separate from each other and a first short closely wound region 372b in which the adjacent wire portions 32a are applied with a tight contact force based on an initial tensile force. The first short sparsely wound portion 372a and the first short closely wound portion 372b are alternately arranged. The intervals of the adjacent wire portions 32a of the first short sparsely wound portion 372a are shorter than those of the wire portions 32a of the first sparsely wound region 44 and the sparsely wound portion 54 of the closely wound region 42. With this structure, the first short sparsely wound portion 372b has a higher resilience than those of the first sparsely wound region 44 and the sparsely wound portion 54. In the first short closely wound portion 372b, the tight contact force of the wire portions 32a is decreased from that of the closely wound portion 52. The first short closely wound portion 372a is shorter than the closely wound portion 52 along the longitudinal axis L.

The second region 364 includes a second Short sparsely wound portion 374a in which the adjacent wire portions 32a are separate from each other and a second short closely wound region 374b in which the adjacent wire portions 32a are applied with a tight contact force based on an initial tensile force. The second short sparsely wound portion 374a and the second short closely wound portion 374b are alternately arranged. The intervals of the adjacent wire portions 32a of the second short sparsely wound portion 374a are shorter than those of the wire portions 32a of the first sparsely wound region 44 and the sparsely wound portion 54 of the closely wound region 42. With this structure, the second short sparsely wound portion 372b has a higher resilience than that of the first sparsely wound region 44 and the sparsely wound portion 54. In the second short closely wound portion 374b, the tight contact force of the wire portions 32a is decreased from that of the closely wound portion 52. The first short closely wound portion 374b is shorter than the closely wound portion 52 along the longitudinal axis L.

The intervals of the adjacent wire portions 32a of the second short sparsely wound portion 374a are somewhat shorter than those of the wire portions 32a of the first sparsely wound portion 372a. With this structure, the second short sparsely wound portion 374a has a higher resilience than that of the first sparsely wound region 44 and the first short sparsely wound portion 372a.

In the second short closely wound portion 374b, the tight contact force of the wire portions 32a is increased from that of the first short closely wound portion 372b and is decreased from that of the closely wound portion 52 of the closely wound region 42. The second short closely wound portion 374b is fully shorter than the closely wound portion 52 along the longitudinal axis L.

The change region 50 of the present modification includes a plurality of maintaining regions 362 and 364 in which respective resiliences are maintained constant. The change region 50 decreases the resilience stepwise along the longitudinal axis L in a direction away from a position in the neighborhood of the closely wound region 42.

It is assumed here that the unbendability (resilience) of the outer sheath 34 is constant from the distal end to the proximal end.

The fifth flexible portion 80 includes, from the distal side to the proximal side, a first portion (maintaining region) 382 which is harder to bend than the first flexible portion 72 and a second portion (maintaining region) 384 which is harder to bend than the first portion 382.

In the fifth flexible portion 80, the unbendability and resilience are gradually decreased stepwise from the distal side to the proximal side along the longitudinal direction, from those of the first flexible portion 72 toward those of the second flexible portion 74.

As can be seen, the unbendability of the distal end portion of the fifth flexible portion 80 is made close to the unbendability of the first flexible portion 72, and the unbendability of the proximal end portion of the fifth flexible portion 80 is made close to the unbendability of the second flexible portion 74. In the fifth flexible portion 80, the unbendability is gradually decreased stepwise from the distal side to the proximal side along the longitudinal direction L, from that of the first flexible portion 72 toward that of the second flexible portion 74. In this manner, the fifth flexible portion 80 prevents the resilience from changing greatly between the first and second flexible portions 72 and 74. With this structure, the portion between the first flexible portion 72 and the fifth flexible portion 80 and the portion between the fifth flexible portion 80 and the second flexible portion 74 are prevented from being sharply bent when they are exerted with an external force.

Next, the third embodiment will now be described with reference to FIG. 15. This embodiment is a modification of the first and second embodiments including the respective modifications.

Figure 15:
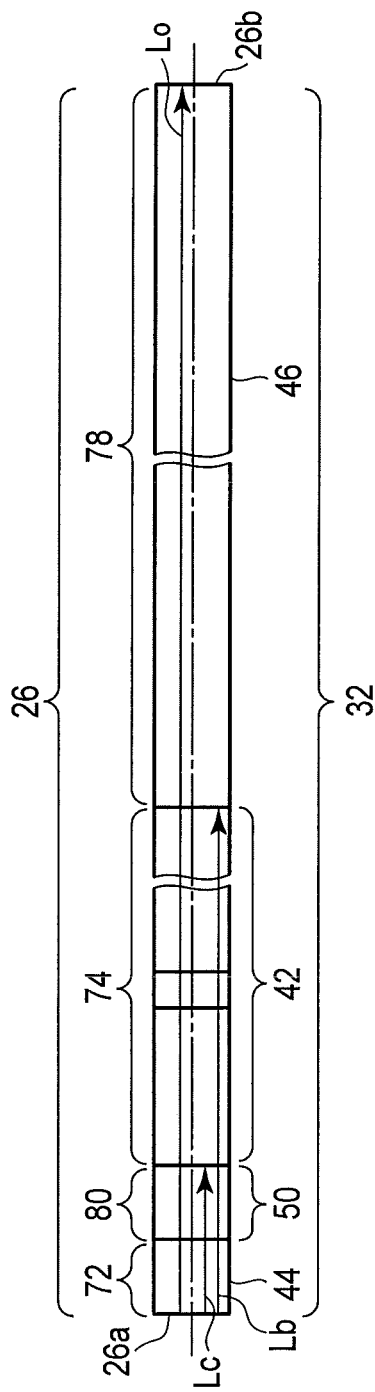
FIG. 15 is a schematic view showing a flexible tube of an insertion section of an insertion apparatus according to the third embodiment.

As shown in FIG. 15, the helical tube 32 includes a first sparsely wound region 44, a closely wound region 42 and a second sparsely wound region 46. The flexible tube 26 of this embodiment does not have such a proximal-end-side change region 48 as is shown in FIG. 12. In other words, the flexible tube 26 comprises, from the distal end to the proximal end, a first flexible portion 72, a fifth flexible portion 80, a second flexible portion 74 and a fourth flexible portion 78. The flexible tube 26 having this structure can be suitably employed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube having a longitudinal axis extending between a distal end and a proximal end, comprising:
   a tubular outer sheath defining a length of the flexible tube; and
   a helical tube comprised of a helical wire with wire windings and including:
   a first sparsely wound region (1) arranged along the longitudinal axis, (2) that includes a first set of the wire windings that are not in contact and are spaced from each other, and (3) forming a first flexible portion with the outer sheath having a first rigidity;
   a closely wound region (1) arranged along the longitudinal axis, (2) located on a proximal side of the first sparsely wound region along the longitudinal axis, (3) that includes (a) a plurality of second sets of the wire windings that are applied with a tight contact force and which are in tight contact with each other and (b) a third set of the wire windings (i) that is between the plurality of second sets of the wire windings and (ii) in which the wire windings are not in contact with and are spaced from each other along the longitudinal axis, and (4) forming a second flexible portion with the outer sheath having a second rigidity, the closely wound region being (1) more unbendable than the first sparsely wound region and (2) longer than the first sparsely wound region along the longitudinal axis,
   a change region (1) arranged along the longitudinal axis and (2) forming a third flexible portion with the outer sheath, wherein the third flexible portion has a third rigidity that varies between a distal end portion and a proximal end portion of the third flexible portion; and
   a second sparsely wound region (1) arranged along the longitudinal axis, (2) located on a proximal side of the closely wound region, (3) that includes a fourth set of the wire winding that are spaced from each other, and (4) forming a fourth flexible portion with the outer sheath having a fourth rigidity, the second sparsely wound region being more bendable than the closely wound region,
   wherein:
     the second rigidity is more rigid then the first rigidity and the fourth rigidity;
     the first sparsely wound region, the closely wound region, the change region and the second sparsely wound region are separate regions axially along the longitudinal axis;
     when the change region is between the closely wound region and the second sparsely wound region, the third rigidity of the third flexible portion varies between (1) a distal end rigidity at the distal end portion of the third flexible portion that is close to the second rigidity of the second flexible portion and (2) a proximal end rigidity at the proximal end portion of the third flexible portion that is close to the fourth rigidity of the fourth flexible portion;
     when the change region is between the first sparsely wound region and the closely wound region, the third rigidity of the third flexible portion varies between (1) the distal end rigidity at the distal end portion of the third flexible portion that is close to the first rigidity of the first flexible portion and (2) the proximal end rigidity at the proximal end portion of the third flexible portion that is close to the second rigidity of the second flexible portion; and
   the outer sheath is harder to bend at a first part around the second sparsely wound region than at a second part around the closely wound region.

2. The flexible tube according to claim 1, wherein:
   the change region includes a plurality of maintaining regions;
   each of the plurality of maintaining regions has a different rigidity; and
   the rigidity of the plurality of maintaining regions varies stepwise along the longitudinal axis.

3. The flexible tube according to claim 2, wherein the maintaining regions include, from a position close to the closely wound region to a position farther from the closely wound region along the longitudinal axis:
   a first region in which the wire windings are equally spaced, and which is easier to bend than the second flexible portion; and
   a second region in which the wire windings are equally spaced, and which is easier to bend than the first region and harder to bend than the fourth flexible portion.

4. The flexible tube according to claim 2, wherein the maintaining regions are configured such that spaces between the wire windings in the maintaining regions increase in accordance with an increase in a distance from the closely wound region along the longitudinal axis.

5. The flexible tube according to claim 1, wherein the change region is configured such that spaces between the wire windings in the change region increase in accordance with an increase in a distance from the closely wound region along the longitudinal axis.

6. The flexible tube according to claim 1, wherein the second flexible portion exhibits a higher resilience than the first flexible portion and the fourth flexible portion when the flexible tube is bent, and
   a resilience of the third flexible portion decreases in accordance with an increase in a distance from the second flexible portion along the longitudinal direction.

7. An insertion apparatus comprising the flexible tube as defined in claim 1.

8. A flexible tube having a longitudinal axis extending between a distal end and a proximal end and including a helical tube comprised of a helical wire with wire windings, the helical tube comprising:
   a first sparsely wound region (1) arranged along the longitudinal axis, (2) that includes a first set of the wire windings that are not in contact and are spaced from each other, and (3) forming a first flexible portion having a first rigidity;
   a closely wound region (1) arranged along the longitudinal axis, (2) located on a proximal side of the first sparsely wound region along the longitudinal axis, (3) that includes (a) a plurality of second sets of the wire windings, that are applied with a tight contact force and which are in tight contact with each other and (b) a third set of the wire windings (i) that is between the plurality of second sets of the wire windings and (ii) in which the wire windings and are not in contact with and are spaced from each other along the longitudinal axis, and (4) forming a second flexible portion having a second rigidity that is more rigid than the first flexible portion;

a change region (1) arranged along the longitudinal axis and (2) forming a third flexible portion, wherein the third flexible portion has a third rigidity that varies between a distal end portion and a proximal end portion; and a second sparsely wound region (1) arranged along the longitudinal axis, (2) located on a proximal side of the closely wound region, (3) that includes a fourth set of the wire windings, that are spaced from each other, and (4) forming fourth flexible portion which is less rigid than the first flexible portion; wherein:

the change region includes:

a first portion located adjacent to the closely wound region;

a second portion located farther from the closely wound region than the first portion, wherein the wire windings in the second portion have a tight contact force equal to or lower than the tight contact force of wire windings in the first portion, and a third portion arranged between the first and second portions and being harder to bend than the first and second sparsely wound regions;

the third portion is equal to or shorter than each of the first portion and the second portion along the longitudinal axis; and the first sparsely wound region, the closely wound region, the change region and the second sparsely wound region are separate regions along the longitudinal axis.

9. The flexible tube according to claim 8, comprising a tubular outer sheath which defines a length of the flexible tube, wherein:

the first sparsely wound region cooperates with the outer sheath to form the first flexible portion, the closely wound region cooperates with the outer sheath to form the second flexible portion, the change region cooperates with the outer sheath to form the third flexible portion, and the second sparsely wound region cooperates with the outer sheath to form the fourth flexible portion.

10. The flexible tube according to claim 9, wherein:

when the change region is between the closely wound region and the second sparsely wound region, the third rigidity of the third flexible portion varies between (1) a distal end rigidity at the distal end portion of the third flexible portion that is close to the second rigidity of the second flexible portion and (2) a proximal end rigidity at the proximal end portion of the third flexible portion that is close to the fourth rigidity of the fourth flexible portion, and when the change region is between the first sparsely wound region and the closely wound region, the third rigidity of the third flexible portion varies between (1) the distal end rigidity at the distal end portion of the distal end portion of the third flexible portion that is close to the first rigidity of the first flexible portion and (2) the proximal end rigidity at the proximal end portion of the third flexible portion that is close to the second rigidity of the second flexible portion.

11. The flexible tube according to claim 8, wherein the change region includes a fourth portion which is farther from the closely wound region than the second portion, and which is easier to bend than the third portion and harder to bend than the first and second sparsely wound regions.

* * * * *